US008329676B2

(12) United States Patent
Lynch et al.

(10) Patent No.: US 8,329,676 B2
(45) Date of Patent: Dec. 11, 2012

(54) CYCLOALKANE-CONTAINING SPHINGOSINE 1-PHOSPHATE AGONISTS

(75) Inventors: Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 12/834,884

(22) Filed: Jul. 12, 2010

(65) Prior Publication Data
US 2011/0245204 A1 Oct. 6, 2011

Related U.S. Application Data

(62) Division of application No. 11/816,258, filed as application No. PCT/US2006/005304 on Feb. 14, 2006, now Pat. No. 7,754,703.

(60) Provisional application No. 60/652,642, filed on Feb. 14, 2005, provisional application No. 60/669,616, filed on Apr. 8, 2005, provisional application No. 60/692,760, filed on Jun. 22, 2005.

(51) Int. Cl.
*A61K 31/661* (2006.01)
*A61K 31/133* (2006.01)
*C07F 9/09* (2006.01)
*C07C 215/44* (2006.01)
(52) U.S. Cl. ........... 514/114; 514/647; 564/15; 564/307
(58) Field of Classification Search .............. 514/114, 514/647; 564/15, 307
See application file for complete search history.

(56) References Cited

U.S. PATENT DOCUMENTS

| 4,939,130 | A | 7/1990 | Jaeggi et al. |
| 5,405,988 | A | 4/1995 | Klar et al. |
| 6,069,251 | A | 5/2000 | Thurkauf et al. |
| 6,875,757 | B2 | 4/2005 | Miller et al. |
| 7,060,697 | B2 | 6/2006 | Marsilje et al. |
| 7,064,217 | B2 | 6/2006 | Macdonald et al. |
| 7,241,790 | B2 | 7/2007 | Lynch et al. |
| 2004/0224941 | A1 | 11/2004 | Seko et al. |
| 2005/0032744 | A1 | 2/2005 | Michaelis et al. |
| 2005/0043386 | A1 | 2/2005 | Nishi et al. |
| 2005/0107447 | A1 | 5/2005 | Lynch et al. |
| 2006/0135786 | A1 | 6/2006 | Saha et al. |
| 2006/0223866 | A1 | 10/2006 | Evindar et al. |
| 2007/0088002 | A1 | 4/2007 | Lynch et al. |
| 2007/0191313 | A1 | 8/2007 | Beard et al. |

FOREIGN PATENT DOCUMENTS

| DE | 1 056 139 B | 4/1959 |
| DE | 3544373 A1 | 6/1987 |
| EP | 1 553 091 A1 | 7/2005 |
| GB | 950388 | 2/1964 |
| JP | 2002-316985 | 10/2002 |
| WO | WO 99/35259 | 7/1999 |
| WO | WO 01/60819 A1 | 8/2001 |
| WO | WO0171022 A2 | 9/2001 |
| WO | WO 02/064616 A2 | 8/2002 |
| WO | WO 02/076995 A2 | 10/2002 |
| WO | WO 02/092068 A1 | 11/2002 |
| WO | WO 03/059880 A1 | 7/2003 |
| WO | WO 03/061567 A2 | 7/2003 |
| WO | WO 2004/010949 A2 | 2/2004 |
| WO | WO2004/010987 A2 | 2/2004 |
| WO | WO 2004/017917 A2 | 3/2004 |
| WO | WO 2004/024673 A1 | 3/2004 |
| WO | WO 2004/028521 A2 | 4/2004 |
| WO | WO 2004/096752 A1 | 11/2004 |
| WO | WO2004103279 A2 | 12/2004 |
| WO | WO2004103306 A2 | 12/2004 |
| WO | WO 2005/032465 A2 | 4/2005 |
| WO | WO 2005/041899 A2 | 5/2005 |
| WO | WO2006001463 A1 | 1/2006 |
| WO | WO2006020951 A1 | 2/2006 |
| WO | WO2006063033 A2 | 6/2006 |
| WO | WO2006088944 A1 | 8/2006 |
| WO | WO 2007/085451 A2 | 8/2007 |
| WO | WO 2007/086001 A2 | 8/2007 |
| WO | WO 2007/091396 A1 | 8/2007 |

OTHER PUBLICATIONS

Brinkmann, FTY720 (fingolimod) in Multiple Sclerosis: therapeutic effects in the immune and the central nervous system, 2009, British Journal of Pharmacology, 158, p. 1173-1182.*
Hla, Physiological and pathological actions of sphingosine 1-phosphate, 2004, Seminars in Cell & Developmental Biology, vol. 15, 513-520.*
Hu, Sphingosine-1-phosphate: a potential therapeutic target for rheumatoid arthritis, 2011, Mol. Biol. Rep, vol. 38, p. 4225-4230.*
Rapizzi, Sphingosine 1-phosphate increases glucose uptake through trans-activation of insulin receptor, 2009, Cellular and Molecular Life Sciences, vol. 66, p. 3207-3218.*
"Uveitis", http://www.ncbi.nlm.nih.gov/pubmedhealth/PMH0002000/, accessed Nov. 10, 2011.*
International Search Report for PCT/US2006/005304 (Jul. 7, 2006).
Bandini, M. et al., "An Effective and Useful Synthesis of Enantiomerically Enriched Arylglycinols", *Eur. J. Chem.* 2001,1937-1942.
Beilstein, XP-002380276, 1985.
Bertus, P. et al., "New and easy route to primary cyclopropylamines from nitriles",*Chem Commun*, 2001,1792-1793.
Brinkmann, V. et al., "FTY720: Altered Lymphocyte Traffic Results in Allograft Protection", *Transplantation* 72, 2001, 764-769.
Brinkmann, V. et al., "The Immune Modulator FTY720 Targets Sphingosine 1-Phosphate Receptors", *J Biol Chem* 277, 2002, 21453-21457.

(Continued)

*Primary Examiner* — Golam M M Shameem
*Assistant Examiner* — Karen Cheng
(74) *Attorney, Agent, or Firm* — J.A. Lindeman & Co., PLLC

(57) ABSTRACT

The present invention provides sphingosine-1-phosphate analogs that are potent, and selective agonists at one or more S1P receptors, specifically the $S1P_1$ receptor type, which alter lymphocyte trafficking. The compounds of the invention include compounds having a phosphate moiety as well as compounds with hydrolysis-resistant phosphate surrogates such as phosphonates, alpha-substituted phosphonates, and phosphothionates.

19 Claims, 19 Drawing Sheets

OTHER PUBLICATIONS

Burger, A. et al., "1-Methyl-2-phenylcyclopropylamine", *Journal of Medicine and Pharmaceutical Chemistry*, vol. 4, No. 3, 1961.

Chiba, K. et al., "FTY720, a Novel Immunosuppressant, Induces Sequestration of Circulating Mature Lymphocytes by Acceleration of Lymphocyte Homing in Rats. I. FTY720 Selectively Decreases the Number of Circulating Mature Lymphocytes by Acceleration of Lymphocyte Homing", *J Immunol* 160, 1998, 5037-5044.

Choi, D. et al., "Synthesis and Anticonvulsant Activities of N-Benzyl-2-acetamidopropionamide", *J Med Chem* 39, 1996, 1907-1916.

Clair, T. et al., "Autotaxin Hydrolyzes Sphingosylphophorylcholine to Produce the Regulator of Migration, Sphingosine-1-Phosphate", *Cancer Res* 63, 2003, 5446-5453.

Clemens, J. et al., "Synthesis of Para-Alkyl Aryl Amide Analogues of Sphingosine-1-phosphate: Discovery of Potent SIP Receptor Agonists", *Bioorg Med Chem Lett* 13, 2003, 3401-3404.

Clemens, J. et al., "Synthesis of 4(5)-phenylimidazole-based analogs of sphingosine-1-phosphate and FTY720: Discovery of potent S IP1 receptor aaonists", *Bioorganic & Medicinal Chemistry Letters* 15, 2005, 3568-3572.

Crosignani, S. et al., "4-Naphthyl-Substituted Bis(Oxazoline): a New Easily Recoverable and Efficient Chiral Ligand in Asyrnetric Catalysis of the Diels-Alder Reaction", *Tetrahedron* 54, 1998, 15721-15730.

Davis, M. et al. "Sphingosine 1-Phosphate Analogs as Receptor Antagonists", *The Journal of Biological Chemistry*, vol. 280, No. 11, 2005, 9833-9841.

Forrest, M. et al., "immune Cell Regulation and Cardiovascular Effects of Sphingosine 1-Phophate Receptor Agonists in Rodents are Mediated via Distinct Receptor Subtypes", *Pharmacol Exp Ther* 309, 2004, 758-768.

Foss, F. et al., "Synthesis, stability, and implications of phosphothioate agonists of sphingosine-1-phosphate receptors", *Bioorganic & Medicinal Chemistry* 15, 2005, 4470-4474.

Foss, F. et al., "Synthesis and biological evaluation of ☐-aminophosphonates as potent, subtype-selective sphingosine 1-phosphate receptor agonists and antagonists", *Bioorganic & Medicinal Chemistry* 15, 2007, 663-677.

Fujino, M. et al. "Amelioration of Experimental Autoimmune Encephalomyelitis in Lewis Rats by FTY720 Treatment", *J Pharmacol Exp Ther* 305, 2003, 70-77.

Graler, M. H. et al., "The immunosuppressant FTY720 down-regulates sphingosine1-phosphate G-protein-coupled receptors", *FASEB* 18, 2004, 551-553.

Hale, Jeffrey J. et al., "Potent S1P receptor agonists replicate the pharmacologic actions of the novel immune modulator FTY720", *Bioorganic & Medicinal Chemistry Letters* 14, 2004, 3351-3355.

Hale, J. J. et al., "Selecting against $S1P_3$ enhances the acute cardiovascular tolerability of 3-(n-benzyl)aminopropylphosphonic acid S1P receptor agonists", *Bioorg Med Chem Lett* 14, 2004, 3501-3505.

Hale, J. J. et al., "The discovery of 3-(N-alkyl)aminopropyiphosphonic acids as potent S1P receptor agonists", *Bioorg Med Chem Lett* 14, 2004, 3495-3499.

Hale, J. J. et al., "A Rational Utilization of High-Throughput Screening Affords Selective, Orally Bioavailable 1-Benzyl-3-carboxyazetidine Sphingosine-1-phosphate-1 Receptor Agonists", *J Med Chem*, 2004, 47, 6662-6665.

Hanessian, S. et al., "Constrained azacyclic analogues of the immunomodulatory agent FTY270 as molecular probes for sphingosine 1-phosphate receptors", *Bioorganic & Medicinal Chemistry Letters* 17, 2007, 491-494.

Hoshino, Y. et al., "FTY720, A Novel lmmunosuppressant, Shows a Synergetic Effect in Combination With FK 506 in Rat Allograft Models", (1999) *Transplant Proc* 31, 1224-1226.

Im, D. S. et al., "Characterization of a Novel Sphingosine 1-Phosphate", (2000) *J Biol Chem* 275, 14281-14286.

Im, D. S. et al., "Characterization of the Human and Mouse Sphingosine 1-Phosphate Receptor, $SIP_5$ (Edg-8): Structure—Activity Relationship of Sphingosine 1-Phosphate Receptors", *Biochemistry* 40, 2001, 14053-14060.

Jones, L. et al., "Rapid Solution and Solid Phase Synthesis of Oligo (1,4-phrenylene ethynylene) with Thioester Termini: Molecular Scale Wires with Alligator Clips. Derivation of Iterative Reaction Efficiencies on a Polymer Support", (1997) *J Org Chem* 62, 1388-1410.

Kaiser, C. et al., "2-Substituted Cyclopropylamines. I. Derivatives and Analogs of 2-Phenylcyclopropylamine", XP009032189, Nov. 1962, 1243-1265.

Kawasaki, K. et al., "Enantioselective Allylic Oxidation of Cycloalkenes by Using Cu(II)-Tris(oxazoline) Complex as a Catalyst", *Tetrahedron*, vol. 53, No. 18, 1997, 6337-6350.

Kharel, Y. et al., "Sphingosine Kinase 2 Is Required for Modulation af Lymphocyte Traffic by FTY 720", *J Bio Chem*, vol. 280, No. 44, Nov. 4, 2005, 36865-36872.

Kimura, T. et al., "High-Density Lipoprotein Stimulates Endothelial Cell Migration and Survival Through Sphingosine 1-Phosphate and Its Receptors", (2003) *Arterioscler Thromb Vasc Biol* 23, 1283-1288.

Kiuchi, M. et al., "Synthesis and immunosuppressive Activity of 2-Substituted 2-Aminopropane-1,3-diols and 2-Aminoethanols[1,2]", (2000) *J Med Chem* 43, 2946-2961.

Kon, J. et al., "Comparison of intrinsic Activities of the Putative Sphingosine 1-Phosphate Receptor Subtypes to Regulate Several Signaling Pathways in Their cDNA-transfected Chinese Hamster Ovary Cells", (1999) *J Bio Chem* 274, 23940-23947.

Lee, M. J. et al., "Sphingosine-1-Phosphate as a Ligand for the G Protein-Coupled Receptor EDG-1", (1998) *Science* 279, 1552-1555.

Lew, M. J. et al., "Analysis of competitive agonist-antagonist interactions by nonlinear regression", (1995) *Trends Pharmacoi Sci* 16, 328-337.

Li, Z. et al., "Discovery of Potent 3,5-Diphenyl-1,2,4-oxadiazole Sphingosine-1-phosphate-1 ($S1P_1$) Receptor Agonists with Exceptional Selectivity against $S1P_2$ and $S1P_3$", *Journal of Medicinal Chemistry*, vol. 48, No. 20, Oct. 6, 2005, 6169-6173.

Maki, T. et al., "Prevention of Autoimmune Diabetes by FTY720 in Nonobese Diabetic Mice", (2002) *Transplantation* 74, 1684-1686.

Maki, T. et al., "Prevention and Cure of Autoimmune Diabetes in Nonobese Diabetic Mice by Continuous Administration of FTY720", (2005) *Transplantation* 79, 1051-1055.

Mandala, S. et al., "Alteration of Lymphocyte Trafficking by Sphingosine 1-Phosphate Receptor Agonists", (2002) *Science* 296, 346-349.

Matloubian, M. et al., "Lymphocyte egress from thymus and peripheral lymphoid organs is dependent on S1P receptor 1",(2004) *Nature* 427, 355-360.

Sanchez, T. et al., "Phosphorylation and Action of the immunomodulator FTY720 Inhibits Vascular Endothelial Cell Growth Factor-induced Vascular Permeability", (2003) *J Biol Chem* 278, 47281-47290.

Sanna, M. G. et al., "Sphingosine 1-Phosphate (S1P) Receptor Subtypes $S1P_1$ and $S1P_3$, Respectively, Regulate Lymphocyte Recirculation and Heart Rate", (2004) *J Biol Chem* 279, 13839-13848.

Sanna, M. G. et al., "Enhancement of capillary leakage and restoration of lymphocyte egress by a chiral $S1P_1$ antagonist in vivo", *Nature Chemical Biology*, vol. 2, Aug. 2006, 434-441.

Suzuki, S. et al., "Immunosuppressive effect of a drug, FTY720, on lymphocyte responses in vitro and cardiac allograft survival in rats", (1996) *Transpl Immunol* 4, 252-255.

Van Brocklyn, J. R. et al., "Sphingosine 1-Phosphate-induced Cell Rounding and Neurite Retraction are Mediated by the G Protein-coupled Receptor H218", (1999) *J Biol Chem* 274, 4626-4632.

Vogler, R. et al., "Sphingosine-1-Phosphate and Its Paradoxical Effects on Critical Parameters of Cutaneous Wound Healing", *The Journal of Investigative Dermatology*, vol. 48, No. 20, 2005, 6169-6173.

Xie, J. H. et al., "Sphingosine-1-Phosphate Receptor Agonisrn Impairs the Efficiency of the Local Immune Response by Altering Trafficking of Naive and Antigen-Activated $CD4^+$ T Cells", (2003) *J Immunol* 170, 3662-3670.

Yanagawa, Y. et al., "The significance of timing of FTY720 administration on the immunosuppressive effect to prolong rat skin allograft survival", (2000) *Int J Immunopharmacol* 22, 597-602.

Yanagawa, Y. et al., "FTY720, a Novel Immunosuppressant, Prolongs Rat Skin Allograft Survival by Decreasing T-Cell Infiltration into Grafts", (1999) *Transplant Proc* 31, 1227-1229.

Yang, Z., et al. "The immune modulator FYT720 prevents autoimmune diabetes in nonobese diabetic mice", (2003) *Clin Immunol* 107, 30-35.

Zhang, T. et al., "Concurrent Overexpression of Cyelin D1 and Cyelindependent Kinase 4 (Cdk4) in Intestinal adenomas from Multiple Intestinal Neoplasia Mice and Human Familial Adenomatous Polyposis Patients", (1997) *Cancer Res* 57, 169-175.

Zhang, Y. H. et al., "Sphingosine-1-Phosphate Via Activation of a G-Protein-Coupled Receptor(s) Enhances the Excitability of Rat Sensory Neurons", *J Neurophysiol* 196, 2006, 1042-1052.

Zhang, Y. H. et al., "Intracellular sphingosine 1-phosphate mediates the increased excitability produced by nerve growth factor in rat sensory neurons", *J Physio* 1575, 2006,101-113.

\* cited by examiner

CYCLOALKANE-CONTAINING SPHINGOSINE 1-PHOSPHATE AGONISTS

CROSS-REFERENCE TO RELATED APPLICATIONS

This application is a division of U.S. application Ser. No. 11/816,258 filed May 6, 2008, which is a National Stage Entry of International Application Serial No. PCT/US06/05304, filed Feb. 14, 2006, published as WO2006/088944, Aug. 24, 2006, which claims Priority from U.S. Provisional Application Provisional Application Nos. 60/652,642, filed Feb. 14, 2005, 60/669,616, filed Apr. 8, 2005 and 60/692,760, filed Jun. 22, 2005, the disclosures of all of which are incorporated by reference in their entirety.

US GOVERNMENT RIGHTS

This invention was made with United States Government support under Grant Nos. RO1 GM067958 and RO1 GM052722 awarded by the National Institutes of Health. The United States Government has certain rights in the invention.

FIELD OF THE INVENTION

The present invention relates to novel sphingosine 1-phosphate analogs with activity at one or more sphingosine 1-phosphate receptors.

BACKGROUND

Sphingosine 1-phosphate (SIP) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers.

Sphingosine 1-phosphate (S1P) evokes many responses from cells and tissues. Prominent among these are resistance to apoptosis, changes in cell morphology, cell migration, cell division, angiogenesis and modulation of the immune system via alterations of lymphocyte trafficking. Therefore, S1P receptors are targets for therapy of, for example, neoplastic diseases, autoimmune disorders and rejection of tissue allografts. Sphingosine-1-phosphate signals cells in part via a set of G protein-coupled receptors named $S1P_1$, $S1P_2$, $S1P_3$, $S1P_4$, and $S1P_5$. These receptors share 50-55% identical amino acids and cluster with three other receptors ($LPA_1$, $LPA_2$, and $LPA_3$) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins re-associate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and S1P lyase is lacking. S1P is released during platelet aggregation, accumulates in serum, and is also found in malignant ascites. Reversible biodegradation of S1P is believed to proceed via hydrolysis by ecto-phosphatases such as the S1P phosphohydrolase, S1P is degraded irreversibly by S1P lyase.

The physiologic implications of stimulating individual S1P receptors are largely unknown due in part to a lack of receptor type selective ligands. Isolation and characterization of S1P analogs that have potent agonist or antagonist activity for S1P receptors has been limited due to the complication of synthesis derived from the lack of solubility of S1P analogs.

Currently, there is a need for novel, potent, and selective agents which are agonists of the S1P receptor. There is also a need for pharmacological tools for the further study of the physiological processes associated with agonism of the S1P receptors.

SUMMARY

The present invention provides sphingosine-1-phosphate analogs that are potent, and selective agonists at one or more S1P receptors, specifically the $S1P_1$ receptor type. The compounds invention include compounds having a phosphate moiety as well as compounds with hydrolysis-resistant phosphate surrogates such as phosphonates, alpha-substituted phosphonates (particularly where the alpha-substitution is a halogen), and phosphothionates. In addition, the invention provides pro-drugs, such as, primary alcohol containing compounds that are activated or converted, (e.g., phosphorylated) in vitro, e.g., by sphingosine kinase enzyme, most particularly sphingosine kinase type 2 (SPHK2).

Accordingly the invention provides sphingosine-1-phosphate analogs having formula (I) or formula (II):

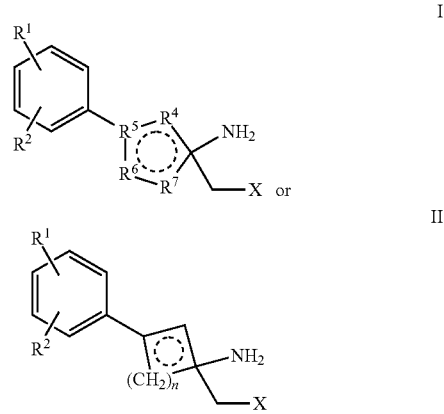

wherein $R^4$ and $R^7$ are independently CH, or $CH_2$; $R^5$ is C, CH, or N, $R^6$ is CH, $CH_2$, O, S or $NR^3$; $R^3$ is hydrogen, or an alkyl group;

X is selected from hydroxyl (—OH), phosphate (—$OPO_3H_2$), phosphonate (—$CH_2PO_3H_2$), alpha-substituted phosphonate;

$R^1$ is selected from the group consisting of hydrogen, halo, tri-fluoromethyl, ($C_1$-$C_{10}$)-alkyl, ($C_1$-$C_{10}$) alkyl substituted with halo, hydroxy, alkoxy, or cyano;

$R^2$ is selected from the group consisting of ($C_1$-$C_{20}$)alkyl, cycloalkyl substituted alkyl, ($C_2$-$C_{20}$)alkenyl, ($C_2$-$C_{20}$)alkynyl, aryl, alkyl substituted aryl, arylalkyl, and aryl substituted arylalkyl; wherein one or more of the carbon atoms in the $R^2$ groups can be independently replaced with non-peroxide oxygen, sulfur or $NR^8$; wherein $R^8$ is hydrogen, or an ($C_1$-$C_{10}$) alkyl group;

wherein the alkyl, alkenyl, and alkynyl groups in $R^2$ are optionally substituted with oxo; n is 0, 1, 2 or 3; and ◯ represents 1, 2, or 3, optional double bonds; or a pharmaceutically acceptable salt or ester thereof.

The present invention also provides esters of any of the compounds of formula (I) or formula (II), e.g., phosphate esters, wherein the ester function can be added to form pro-drugs to increase oral availability.

The invention also provides compounds of formula (I) or formula (II) for use in medical therapy.

In another aspect, the present invention also provides:

compounds of the invention that can be pro-drugs, i.e., they can be activated by phosphorylation, in the subject, e.g., after administration of the primary alcohol to form a mono-phosphorylated analog. In the active form, some compounds of the invention are agonists at the S1P type 1 receptor, and thus evoke lymphopenia, for up to about seven days, or longer, when introduced into animals;

compounds of the invention that can be selective agonists for the $S1P_1$, $S1P_4$, and $S1P_5$ receptors, and have a long duration of action, e.g., longer than FTY-720 (fingolimod);

a pharmaceutical composition comprising a compound of formula (I), formula (II), or mixtures thereof or pharmaceutically acceptable salts, or esters thereof, and a pharmaceutically acceptable excipient;

a method for prevention or treatment of autoimmune diseases, such as, uveitis, type I diabetes, rheumatoid arthritis, inflammatory bowel diseases, and, more particularly, multiple sclerosis, comprising administering to a mammal (e.g., a human) in need of such treatment, an effective amount of a compound of formula (I), formula (II) or a pharmaceutically acceptable salt thereof;

a method for prevention or treatment of progressive dementia or brain degenerative diseases;

altering lymphocyte trafficking as a method for prolonging allograft survival, for example solid organ transplants, treatment of graft vs. host disease, bone marrow transplantation, etc.;

prevent cancer progression via inhibition of autotoxin, e.g., by preventing or inhibiting angiogenesis in a tumor; or the use of a compound of formula I, formula (II), or a pharmaceutically acceptable salt thereof to prepare a medicament for preventing or inhibiting autoimmune diseases or angiogenesis in a tumor in a mammal (e.g., a human).

The invention also provides novel intermediates and processes disclosed herein that are useful for preparing compounds of formula (I) or formula (II), including the generic and specific intermediates as well as the synthetic processes described in the Charts and Examples herein.

DETAILED DESCRIPTION

Abbreviations

Figure 1:
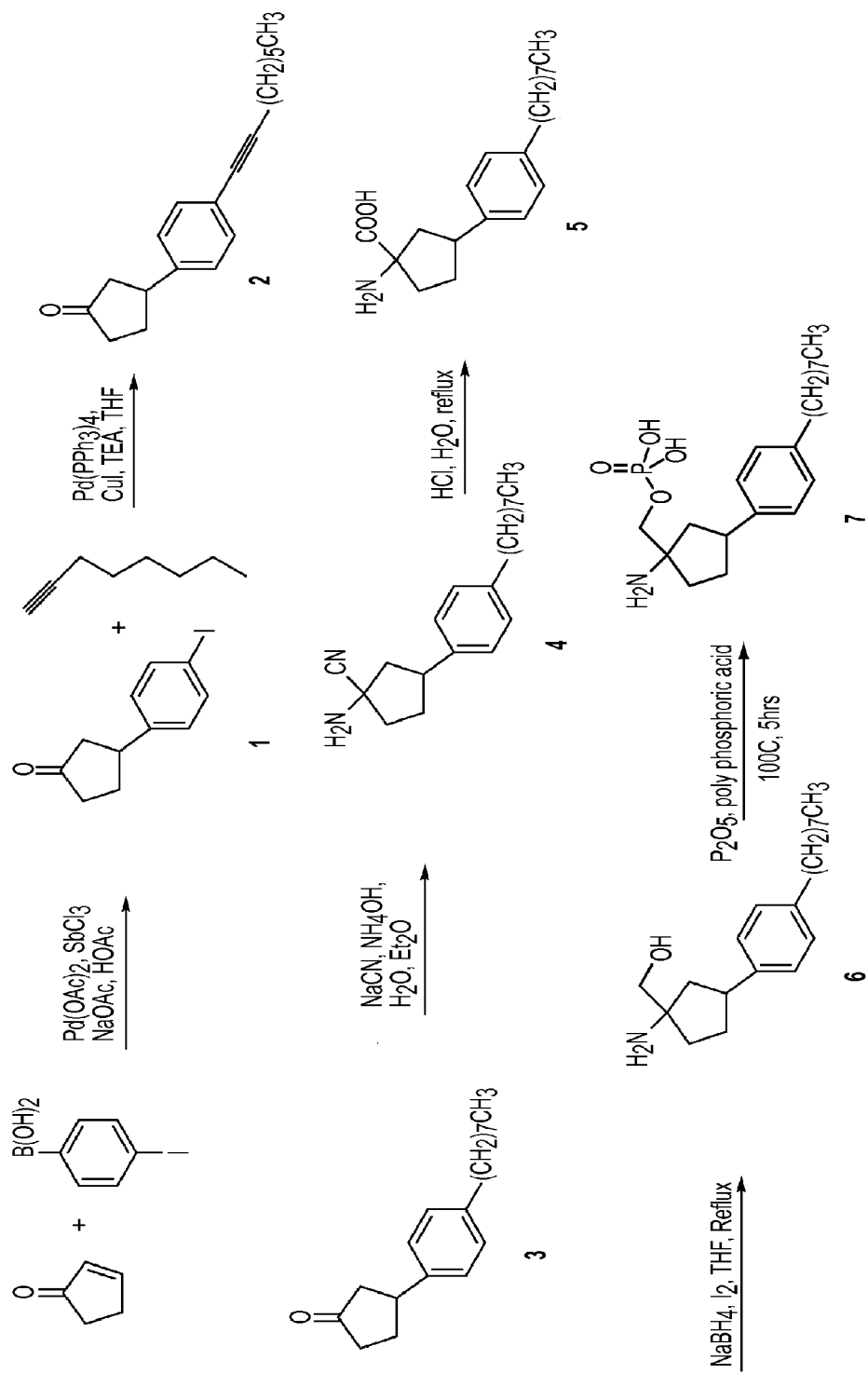
FIG. 1 provides a synthetic route to prepare VPC01091 (6) and to prepare VPC01211 (7).

The following abbreviations are used herein: S1P, sphingosine-1-phosphate; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transciptase polymerase chain reaction Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section.

In describing and claiming the invention, the following terminology will be used in accordance with the definitions set forth below.

For purposes of the description of this invention, the articles "a" and "an" are used herein to refer to one or to more than one (i.e., to at least one) of the grammatical object of the article. By way of example, "an element" means one element or more than one element.

As used herein, an "analog" of a chemical compound is a compound that, by way of example, resembles another in structure but is not necessarily an isomer (e.g., 5-fluorouracil is an analog of thymine).

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

As used herein, a "derivative" of a compound refers to a chemical compound that may be produced from another compound of similar structure in one or more steps, as in replacement of hydrogen by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, an "effective amount" means an amount sufficient to produce a selected effect. A "therapeutically effective amount" of a compound is that amount of compound which is sufficient to provide a beneficial effect to the subject to which the compound is administered.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers known in the art, such as a phosphate buffered saline solution, water, emulsions such as an oil/water or water/oil emulsion, and various types of wetting agents. The term also encompasses any of the agents approved by a regulatory agency of the U.S. Federal government or listed in the US Pharmacopeia for use in animals, including humans.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "subject" of diagnosis or treatment is a mammal, including a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

As used herein, the term "receptor agonists" are defined as compounds that mimic the action of S1P at its receptors but with differing potency and/or efficacy.

As used herein, the term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

As used herein, the term "treating" includes prophylaxis of the specific disorder or condition, or alleviation of the symptoms associated with a specific disorder or condition and/or preventing or eliminating said symptoms.

As used herein, an "effective amount" means an amount sufficient to produce a selected effect. For example, an effective amount of an S1P receptor agonist is an amount that decreases the cell signaling activity of the S1P receptor.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising an inhibitor identified in the invention and an instructional material which describes administering the inhibitor or a composition comprising the inhibitor to a cell or an animal. This should be construed to include other embodiments of kits that are known to those skilled in the art, such as a kit comprising a (preferably sterile) solvent suitable for dissolving or suspending the composition of the invention prior to administering the compound to a cell or an animal. Preferably the animal is a human.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine S1P agonist activity using the standard tests described herein, or using other similar tests which are well known in the art.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of organic (e.g., carboxylic) acids can also be made.

Processes for preparing compounds of formula (I), formula (II) or for preparing intermediates useful for preparing compounds of formula (I) or formula (II) are provided as further embodiments of the invention. Intermediates useful for preparing compounds of formula (I) or formula (II) are also provided as further embodiments of the invention.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "alkyl or $C_1$-$C_{10}$ alkyl," as used herein, represents a branched or linear alkyl group having from one to six carbon atoms. Typically $C_1$-$C_{10}$ alkyl groups include, but are not limited to, methyl, ethyl, n-propyl, iso-propyl, butyl, iso-butyl, sec-butyl, tert-butyl, pentyl, hexyl, heptyl, octyl, and the like.

The term "alkenyl or $C_2$-$C_{10}$ alkenyl," as used herein, represents an olefinically unsaturated branched or linear group having from 2 to 10 carbon atoms and at least one double bond. Examples of such groups include, but are not limited to, 1-propenyl, 2-propenyl, 1,3-butadienyl, 1-butenyl, hexenyl, pentenyl, and the like.

The term "alkynyl or $C_2$-$C_{10}$ alkynyl," refers to an unsaturated branched or linear group having from 2 to 10 carbon atoms and at least one triple bond. Examples of such groups include, but are not limited to, 1-propynyl, 2-propynyl, 1-butynyl, 2-butynyl, 1-pentynyl, and the like.

The term "$C_3$-$C_8$ cycloalkyl," represents cyclopropyl, cyclobutyl, cyclopentyl, cyclohexyl, cycloheptyl, cyclooctyl and the like.

As used herein, the term "optionally substituted" refers to from zero to four substituents, wherein the substituents are each independently selected. Each of the independently selected substituents may be the same or different than other substituents.

As used herein the term "aryl" refers to a mono or bicyclic $C_5$-$C_{10}$ carbocyclic ring system having one or two aromatic rings including, but not limited to, phenyl, benzyl, naphthyl, tetrahydronaphthyl, indanyl, indenyl, and the like.

As used herein "optionally substituted aryl" includes aryl compounds having from zero to four substituents, and a substituted aryl includes aryl compounds having one to three substituents, wherein the substituents include groups such as, for example, alkyl, halo or amino substituents.

The term "arylalkyl" refers to any aryl group which is attached to the parent moiety via the alkyl group, e.g., aryl ($C_1$-$C_8$ alkyl). Thus, the term ($C_5$-$C_6$ aryl)($C_5$-$C_8$ alkyl) refers to a five or six membered aromatic ring that is attached to the parent moiety via the $C_5$-$C_8$ alkyl group.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention can contain one or more asymmetric centers in the molecule. In accordance with the present invention any structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example, the following structure:

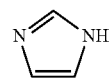

is understood to represent a mixture of the structures:

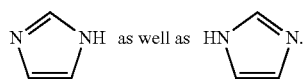

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

As used herein, an "S1P modulating agent" refers a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," as used herein, refers to all of the S1P receptor subtypes (for example, the S1P receptors S1P1, S1P2, S1P3, S1P4, and S1P5), unless the specific subtype is indicated.

As used herein, the term "$EC_{50}$ of an agent" refers to that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% is set at the amount of activity in the assay in the absence of added ligand/agonist.

As used herein, the term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., hydrogen, $NH_4$, Na, and the like if such counterions are present.

The present invention is directed to sphingosine 1-phosphate (SIP) analogs that have activity as receptor agonists at one or more S1P receptors, specifically the $S1P_1$, $S1P_4$ and $S1P_5$ receptor types. The invention includes both compounds that have a phosphate moiety as well as compounds with hydrolysis-resistant phosphate surrogates such as phosphonates, alpha-substituted phosphonates particularly where the alpha substitution is a halogen and phosphothionates.

In one embodiment of the S1P receptor agonists have the general structure of Formula (IIA):

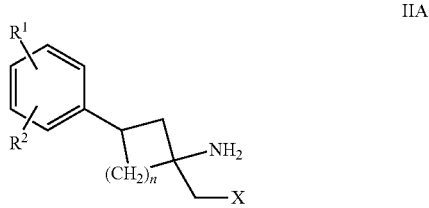

IIA wherein n is 0, 1, 2 or 3; X is selected from hydroxyl (—OH), phosphate (—$OPO_3H_2$), phosphonate (—$CH_2PO_3H_2$), alpha-substituted phosphonate (including: —$CHFPO_3H_2$, —$CF_2PO_3H_2$, —$CHOHPO_3H_2$, —C=$OPO_3H_2$), wherein $R^1$ is selected from the group consisting of hydrogen, halogens (wherein F or Cl are the preferred halogens), ($C_1$-$C_6$) alkyl, such as, methyl, ethyl, and propyl, or halo-, hydroxy-, alkoxy-, cyano-substituted ($C_1$-$C_6$) alkyl, such as, tri-fluoromethyl.

The $R^2$ group is selected from the group consisting of alkyl, alkenyl, alkynyl, alkyl substituted aryl, alkyl substituted cycloalkyl, arylalkyl and arylalkyl substituted aryl. In $R^2$ the chain lengths of 5-8 carbon atoms are preferred; or a pharmaceutically acceptable salt thereof.

The present invention also provides esters of any of the compounds of formula (II), e.g., phosphate esters, wherein the ester function can be added to form pro-drugs to increase oral availability.

In a preferred embodiment, the compounds having formula (II) can have $R^1$ selected from the group consisting of H, halo (F or Cl preferred), methyl, tri-fluoromethyl, ethyl, propyl or other lower alkyl ($C_1$-$C_6$) or halo-, hydroxy-, alkoxy-, cyano-substituted lower alkyl group; and $R_2$ selected from the group consisting of alkyl, alkenyl, alkynyl, alkyl (optionally substituted aryl), alkyl (optionally substituted cycloalkyl), arylalkyl, and arylalkyl (optionally substituted aryl) with chain lengths of 5-8 carbon atoms preferred.

Potential uses of an $S1P_1$ receptor agonist pro-drugs ($S1P_1$ receptor type selective agonists preferred) include, but are not limited to:

Altering lymphocyte trafficking as a method of treatment for autoimmune pathologies such as uveitis, type I diabetes, rheumatoid arthritis, inflammatory bowel diseases, and, most particularly, multiple sclerosis. "Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

In addition, the compounds of the invention can be used for altering lymphocyte trafficking is a method for prolonging allograft survival, for example solid organ transplants, treatment of graft vs. host disease, bone marrow transplantation, and the like.

In addition, the compounds of the invention can be used to inhibit autotaxin. Autotaxin, a plasma phosphodiesterase, has been demonstrated to undergo end product inhibition. Autotaxin hydrolyzes several substrates to yield lysophosphatidic acid and sphingosine 1-phosphate, and has been implicated in cancer progression and angiogenesis. Therefore, S1P receptor agonist pro-drugs such as VPC01091 can be used to inhibit autotaxin. This activity may be combined with agonism at S1P receptors or may be independent of such activity.

In addition, compounds of the invention can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, pro-drugs such as VPC01091 can be used to inhibit S1P lyase. This inhibition could be in concert with S1P receptor activity, or be independent of activity at any S1P receptor.

"Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

The present invention is also includes pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art. For example, a pharmaceutical composition comprising a compound of the invention, or analog, derivative, or modification thereof, as described herein, is used to administer the appropriate compound to a subject.

The compounds of the invention are useful for treating a disease or disorder including administering to a subject in need thereof of a therapeutically acceptable amount of a compound of formula (I), or a pharmaceutical composition comprising a therapeutically effective amount of a compound of formula (I), and a pharmaceutically-acceptable carrier.

A specific value for lower alkyl group is ethyl or propyl.

A specific value for halo is fluorine or chlorine.

A specific value for X is hydroxy or $OPO_3H_2$.

Alpha-substituted phosphonate includes —$CHFPO_3H_2$, —$CF_2PO_3H_2$, —$CHOHPO_3H_2$, —C═$OPO_3H_2$) or thiophosphate ($OPO_2SH_2$).

A specific value for $R^1$ is hydrogen.

A specific value for $R^2$ is an alkyl group with a chain length of 5-8 carbon atoms.

A more specific value for $R^2$ is heptyl, octyl, nonyl, —O-heptyl, —C(═O)heptyl, or $CH_3$—$CH_2$—O—$CH_2$—$CH_2$—O—$CH_2$—$CH_2$—O—.

A more specific value for the alkyl groups in $R^2$ is octyl, or —O-heptyl.

A more specific value for the alkyl groups in $R^2$ is octyl.

A specific value for n is 1 or 2.

Specific cycloalkyl groups having a double bond include:

A specific compound of the invention has $R^2$ group placed para to the cycloalkyl ring.

A specific compound of the invention has the $R^1$ group placed ortho or meta to $R^2$.

A specific compound of the invention has the $R^2$ group placed para to the benzylic cycloalkyl group (i.e., 1,4).

Non-limiting examples of esters of the compounds of the invention include compounds where the X group is;

wherein Y is selected from the group consisting of O, $CH_2$, CHOH, CHF, $CF_2$, and and $R^9$ and $R^{10}$ are independently selected from the group consisting of alkoxy, alkenyloxy, alkynyloxy, aryloxy, wherein $R^{11}$ is selected from the group consisting of $C_1$-$C_4$ alkyl, $C_2$-$C_4$ alkenyl, $C_2$-$C_4$ alkynyl, and optionally substituted aryl. Particularly preferred $R^9$ and $R^{10}$ groups are alkoxy, A synthetic route to prepare VPC01091 and to VPC01211 is provided in the scheme in FIG. 1. Additional compounds of formula (I) or formula (II) can be prepared by a person skilled in the art using known modifications to procedures from the schemes and detailed descriptions in the specific examples herein.

A specific compound of the invention of formula (II) is VPC01091, where X is OH, $R^1$ is hydrogen, $R^2$ is octane ($C_8H_{17}$), n is 2, and the $R^2$ group is in the para position on the phenyl ring. The formula is:

VPC01091

A specific compound of the invention of formula (II) is VPC02162, where X is OH, $R^1$ is hydrogen, $R^2$ is octane ($C_8H_{17}$), n is 2, and the $R^2$ group is in the meta position on the phenyl ring. The formula is:

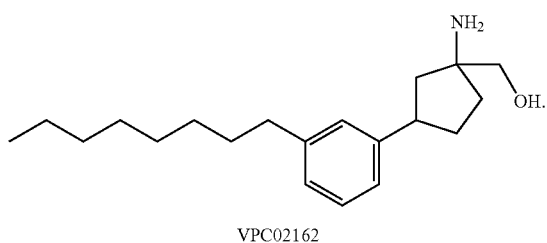

VPC02162

The invention also includes the following isomers:

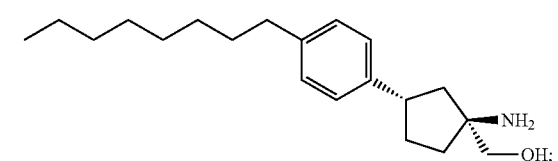

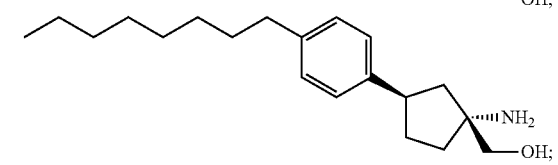

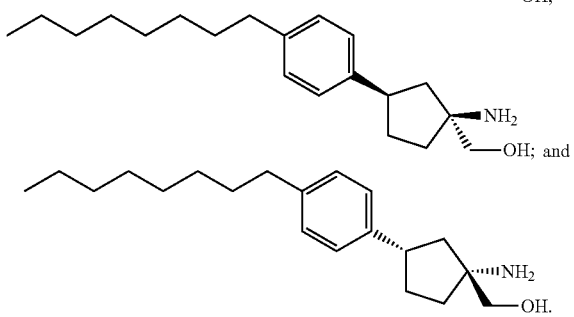

These compounds can be prepared as a mixture and separated by chromatography. Suitable conditions for separation are as follows: Column: Chiralpak AD 4.6 mmID×250 mm; Mobile Phase Hex/EtOH/MeOH/DEA=95/2.5/2.5/0.03; Flow Rate: 1 mL/min; Detector: UV 220 nm; Column Temp: 40° C.; or Column Temp: 25° C. After separation, it was found that two isomers were not phosphorylated by the SPHK2 enzyme in vitro. However, when phosphorylated prior to testing the phosphorylated compounds were found to be active agonists of the S1P receptors.

Another specific compound of the invention of formula (II) is VPC01211 where X is $OPO_3H_2$, $R^1$ is hydrogen, $R^2$ is octane ($C_8H_{17}$), n is 2, and the $R^2$ group is in the para position on the phenyl ring. The formula is:

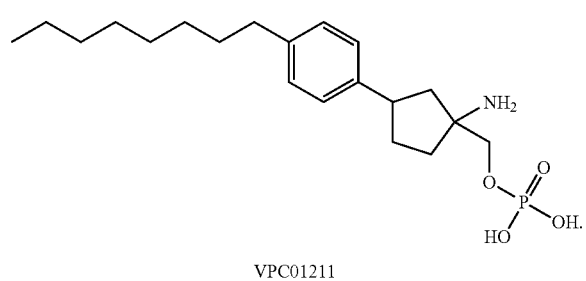

VPC01211

Another specific compound of the invention of formula (II) is VPC02164 where X is $OPO_3H_2$, $R^1$ is hydrogen, $R^2$ is octane ($C_8H_{17}$), n is 2, and the $R^2$ group is in the meta position on the phenyl ring. The formula is:

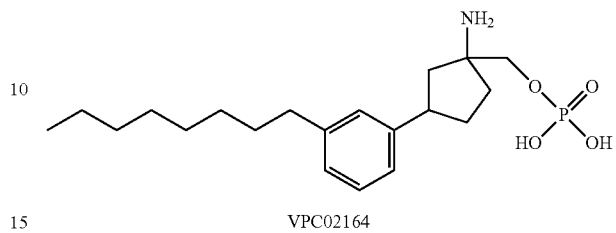

VPC02164

Additional examples of compounds of the invention that include heteroatoms (e.g., N, S, O) and/or double bonds in the cycloalkyl ring include the structures below:

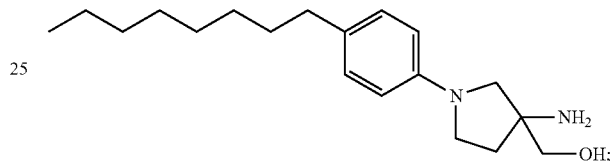

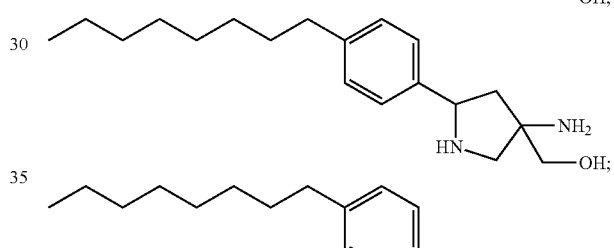

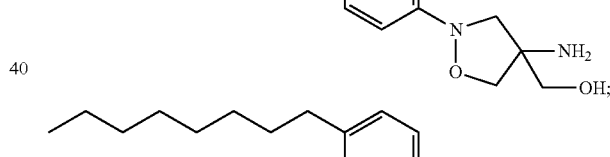

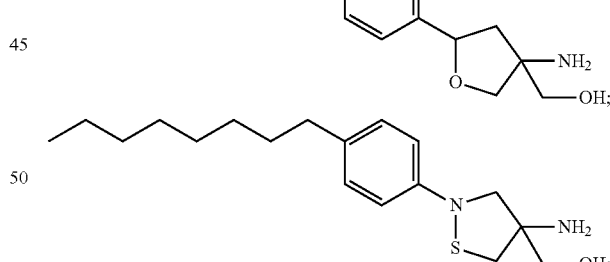

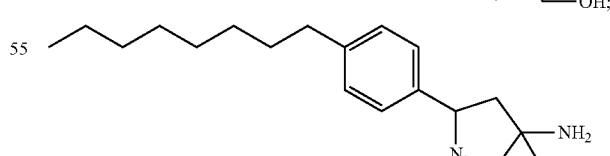

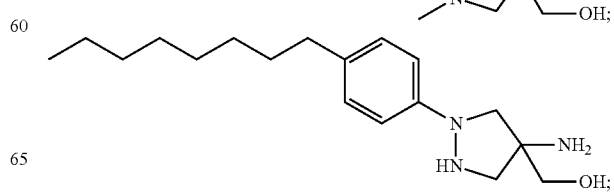

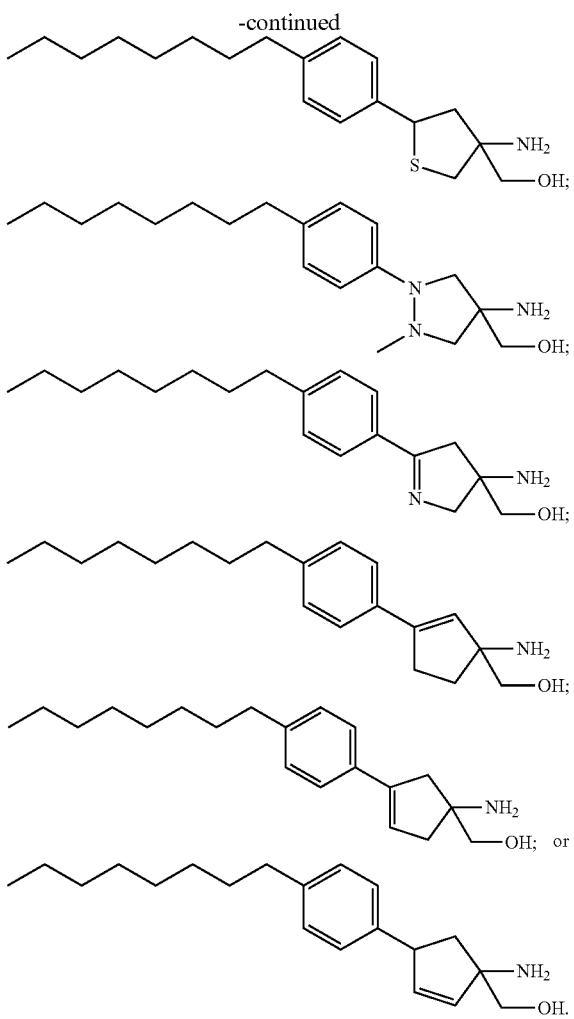

Additional compounds of formula (I) or (II) having the general formula (III) are illustrated below. The specific variables are recited in Table 1:

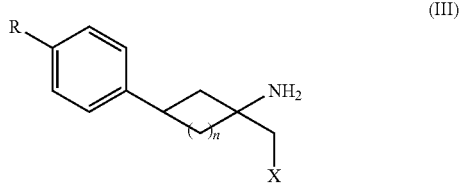

(III)

TABLE 1

| Compound | Fig. Nos. | R | n | X |
|---|---|---|---|---|
| VPC02004 | — | $C_7H_{15}$ | 2 | OH |
| VPC02007 | — | $C_7H_{15}$ | 2 | $OPO_3H_2$ |
| VPC01091 | CA5 | $C_8H_{17}$ | 2 | OH |
| VPC01211 | CA5-P | $C_8H_{17}$ | 2 | $OPO_3H_2$ |
| VPC02031 | — | $C_9H_{19}$ | 2 | OH |
| VPC02033 | — | $C_9H_{19}$ | 2 | $OPO_3H_2$ |
| VPC01289 | — | $C_{10}H_{21}$ | 2 | OH |
| VPC01292 | — | $C_{10}H_{21}$ | 2 | $OPO_3H_2$ |
| VPC01220 | CA4 | $C_8H_{17}$ | 1 | OH |
| VPC01222 | CA4-P | $C_8H_{17}$ | 1 | $OPO_3H_2$ |

TABLE 1-continued

| Compound | Fig. Nos. | R | n | X |
|---|---|---|---|---|
| VPC01213 | CA6 | $C_8H_{17}$ | 3 | OH |
| VPC01214 | CA6-P | $C_8H_{17}$ | 3 | $OPO_3H_2$ |

The invention also provides esters of the compounds of formula (I) or formula (II), where the formation of the ester can convert the compounds to pro-drugs to enhance administration, e.g., increase oral availability. In addition, the invention also provides pharmaceutically acceptable salts of the compounds of formula (I) or formula (II). Further, the invention provide all possible isomers of the structures described by formula (I) or formula (II), noting that when n is one (cyclobutane) the compound is symmetric and lacks chiral centers, but cis and trans forms exist.

Pharmaceutical compositions comprising one of more compounds of the invention can be administered to a subject in need thereof by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. The oral route is typically employed for most conditions requiring the compounds of the invention. Preference is given to intravenous injection or infusion for the acute treatments. For maintenance regimens, the oral or parenteral, e.g. intramuscular or subcutaneous, route is preferred.

In accordance with one embodiment, a composition is provided that comprises a compound of the invention, or an analog, derivative, or modification thereof, and albumin, more particularly, the composition comprises a compound of the present invention, a pharmaceutically acceptable carrier and 0.1-1.0% albumin. Albumin functions as a buffer and improves the solubility of the compounds. In one aspect, albumin is not added.

In one embodiment, the pharmaceutical compositions useful for practicing the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 100 g/kg/day.

Pharmaceutically acceptable carriers which are useful include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides.

Compounds which are identified using any of the methods described herein may be formulated and administered to a subject for treatment of any of the diseases and disorders described herein. However, the use of compounds of the invention should not be construed to include only the diseases and disorder described herein. Preferably, the subject is a human.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals, including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets that are adapted for controlled-release are encompassed by the present invention.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

As used herein, an "oily" liquid is one which comprises a carbon-containing liquid molecule and which exhibits a less polar character than water.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. See Genaro, ed., 1985, Remington's Pharmaceutical Sciences, Mack Publishing Co., Easton, Pa., which is incorporated herein by reference.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type, and age of the subject, etc.

The invention also provides a pharmaceutical pack or kit comprising one or more containers filled with one or more of the ingredients of the pharmaceutical compositions of the invention. In accordance with one embodiment, a kit is provided for treating a subject in need of immuno-modulation. Preferably, the subject is a human. In one embodiment, the kit comprises one or more of the S1P analogs of the present invention and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Although any methods and materials similar or equivalent to those described herein can be used in the practice or testing of the present invention, the preferred methods and materials are described herein.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Example 1

(1-amino-3-(4-octylphenyl)cyclopentyl)methanol (6)

A.: 3-(4-iodophenyl)cyclopentanone (1) 0.23 g palladium (II) acetate (0.1 eq) and 0.23 g antimony(III) chloride (0.1 eq) were added to 80 mL acetic acid solution of 2-cyclopenten-1-one 0.82 g (10 mmol), 4-iodophenylboronic acid 2.48 g (10 mmol) and sodium acetate 1.6 g (20 mmol) under $N_2$ atmosphere. After being stirred for 24 hours at 25° C., the black precipitation was filtered off and the filtrate was diluted with 250 mL of brine, and then extracted twice with 50 mL methylene chloride. The organic extraction was stirred with saturated $NaHCO_3$ solution for 30 minutes, then washed with brine and dried over $MgSO_4$. Removal of solvent resulted in a yellow oil, further purification by flash column (chloroform) gave 1.92 g (67%) product as a white solid. *J. Org. Chem.*, 1995, 60, 883-888.

$^1$H NMR (CDCl$_3$) δ 7.63 (d, 2H, ArH), 7.00 (d, 2H, ArH), 3.35 (m, 1H, ArCHCC), 2.7-1.8 (m, 6H, cyclo-pentyl);

$^{13}$C NMR (CDCl$_3$) δ 218, 143, 138, 129, 95, 46, 42, 39, 31.

B.: 3-(4-(oct-1-ynyl)phenyl)cyclopentanone (2) 1.1 g (10 mmol) of 1-octyne was add to a flame dried 25 mL flask charged with 10 mL THF solution of 1.43 g (5 mmol) of 1. After degassing for 30 minutes, 2 mL triethylamine, 5 mg of CuI and 10 mg of Pd(PPh$_3$)$_4$ were added under N$_2$ protection. The reaction was complete in 6 hrs, after removal of solvent and volatile reagent, the mixture was columned with chloroform to give 1.34 g (99%) yellow oil.

$^1$H NMR (CDCl$_3$) δ 7.35 (d, 2H, ArH), 7.15 (d, 2H, ArH), 3.37 (m, 1H, ArCHCC), 2.7-2.2 (m, 6H, cyclo-pentyl), 1.95 (m, 2H, CCCH$_2$CH$_2$), 1.6-1.2 (m, 8H, CH$_2$), 0.89 (t, J=6 Hz, 2H, CH$_3$);

$^{13}$C NMR (CDCl$_3$) δ 220, 143, 132, 127, 122, 91, 80, 46, 42, 39, 32, 31, 29, 29, 23, 20, 14.

C.: 3-(4-octylphenyl)cyclopentanone (3) Several drops of formic acid and catalytic amount 5% Pd/C was added to a 25 mL flask charged with 10 mL methanol and 1.34 g (5 mmol) of 2. The reaction vessel was flushed with H$_2$, 3 times, and then mounted with a H$_2$ balloon. After two days hydrogenolysis, the solute on wash filter through a pad of silica, then concentrated to yellow oil. 1.32 g (98%) product was collected.

$^1$H NMR (CDCl$_3$) δ 7.18 (s, 4H, ArH), 3.38 (m, 1H, ArCHCC), 2.60 (t, 2H, CCCH$_2$CH$_2$), 2.45-1.91 (m, 6H, cyclo-pentyl), 1.64-1.15 (m, 12H, CH$_2$), 0.90 (t, 3H, CH$_3$);

$^{13}$C NMR (CDCl$_3$) δ 220, 142, 140, 129, 127, 46, 42, 39, 36, 32, 32, 32, 30, 30, 29, 23, 14.

D.: 1-amino-3-(4-octylphenyl)cyclopentanecarbonitrile (4) 3.20 g (11.8 mmol), sodium cyanide 1.15 g (23.5 mmol) and ammonium chloride 1.25 g (23.5 mmol) were added to 20 mL of ammonium hydroxide. The mixture was extracted twice with 10 mL of methylene chloride after vigorously stirring overnight. The organic extraction was dried and concentrated to yellow oil 3.30 g. The crude product is used for next step without further purification. *J. Med. Chem.*, 1986, 29, 1988-1995.

E.: 1-amino-3-(4-octylphenyl)cyclopentanecarboxylic acid (5) 3.3 g (11.2 mmol) and 50 mL concentrated hydrochloric acid was heated to 70° C. and stirred overnight. The resulting clear aqueous solution was evaporated to dryness. 10 mL water was added and dried again. This process was repeated several times. The crude product was washed with water and acetone to give a white fine powder. Yield was 1.7 g (45%).

$^1$H NMR (d$^6$-DMSO) δ 7.25-7.06 (m, 4H, ArH), 3.21 (m, 1H, ArCHCC), 2.38-1.62 (m, 6H, cyclo-pentyl), 1.49-1.20 (m, 14H, CH$_2$), 0.81 (t, J=6 Hz, 3H, CH$_3$);

$^{13}$C NMR (d$^6$-DMSO) δ 175, 141, 140, 64, 51, 46, 45, 44, 36, 35, 35, 34, 32, 32, 29, 29, 23, 15.

F.: (1-amino-3-(4-octylphenyl)cyclopentyl)methanol (6) 63.4 mg (0.2 mmol) 5 and 27 mg (0.6 mmol) sodium borohydride were dissolved in 3 mL of THF. After the solution was cooled to 0° C., 51 mg (0.2 mmol) I$_2$ was dissolved in 1 mL THF and added dropwisely. Then the vessel was fitted with a condenser and the reaction mixture was refluxed under N$_2$ for 5 hrs. Excess NaBH$_4$ was quenched with methanol. After removal of solvent, 2 mL water and 5 mL methylene chloride was added, the mixture was stirred for about 1 hr until the organic layer became clear. The organic phase was collected and aqueous phase was further extracted twice with methylene chloride. The combined organic extraction was dried and concentrated to give 43 mg (71%) crude product. Further purification on TLC with methanol/chloroform (5:95) gave 13 mg clear oil. *J. Org. Chem.*, 1993, 58, 3568-3571.

$^1$H NMR (CD$_3$OD) δ 7.11 (m, 4H, ArH), 3.80 (t, J=7.5 Hz, 1H, c-pentyl-CH$_2$O), 3.67 (t, J=7.5 Hz, 1H, c-pentyl-CH$_2$O), 3.01 (m, 1H, ArCHCC), 2.55 (t, J=7.5 Hz, 2H, ArCH$_2$), 2.29-1.69 (m, 6H, cyclo-pentyl), 1.57 (m, 2H, ArCH$_2$CH$_2$), 1.38-1.28 (m, 10H, CH$_2$), 0.89 (t, J=7.5 Hz, 3H, CH$_3$);

$^{13}$C NMR (CD$_3$COCD$_3$) δ 141, 128, 127, 96, 45, 44, 43, 35, 35, 33, 33, 32, 32, 29, 29, 29, 23, 13.

Example 2

(1-amino-3-(4-octylphenyl)cyclopentyl)methyl dihydrogen Phosphate (7)

(1-amino-3-(4-octylphenyl)cyclopentyl)methyl dihydrogen phosphate (7). 1 mL 85% H$_3$PO$_4$ was slowly drop added into 0.5 g of P$_2$O$_5$, the acid-anhydride mixture was then heated at 100° C. for 1 hour under nitrogen protection. Another 0.5 g of P$_2$O$_5$ and 30 mg of 6 were added to the poly phosphoric acid and heated for 5 hours at 100° C. After cooling down to RT, 10 mL icy cold water was added to reaction mixture. Product precipitated out as white solid. The product was collected and washed with water. 31 mg (82%) green colored product was collected after vacuum dry. MS only two peaks: M+1=384.4 with 304.4 (hydrolyzed back to 6).

Example 3

GTPγS-35 Binding Assay

This assay illustrates agonist activation of G protein coupled receptors (GPCRs) in isolation. The assay forces expression concomitantly of a recombinant GPCR (e.g., the S1P1-5 receptor) and each of the three subunits (typically, alphai2, beta1, gamma2) of a heterotrimeric G protein in a HEK293T cell by transfecting the cell with four plasmid DNAs encoding the respective proteins. About 60 hours after transfection the cells are harvested, opened, and the nucleus discarded. This allows for the preparation of a crude microsome from the remainder. Agonist (e.g., S1P) stimulation of the receptor-G protein complex on the microsomes results in the exchange of GTP for GDP on the alpha subunit in a dose-dependent manner. To detect the GTP-bound alpha subunit, we use a GTP analog (GTPγS-35), which is a radionuclide (sulfur-35) labeled phosphothionate, that is not hydrolyzed to GDP. The microsomes with the adherent G proteins are collected by filtration and the bound GTPγS-35 quantified in a liquid scintillation counter. The assay yields relative potency (EC$_{50}$ values) and maximum effect (efficacy, E$_{max}$). Antagonist activity is detected as rightward shifts in the agonist dose-response curve in the presence of a fixed amount of antagonist. If the antagonist behaves competitively, the affinity of the receptor/antagonist pair (K$_i$) can be determined.

The phosphorylated forms of all the VPC01091 isomers, and phosphorylated VPC01091 (VPC01211, CA5-P) itself are negative, or inverse, agonists at S1P$_3$ receptor and, relative to S1P are partial agonists (i.e., not fully efficacious) at the S1P$_1$ receptor in this assay. Inverse agonists are antagonists, i.e., they will interfere with the binding of agonist ligands, but not evoke an activation of the receptor.

Figure 6:
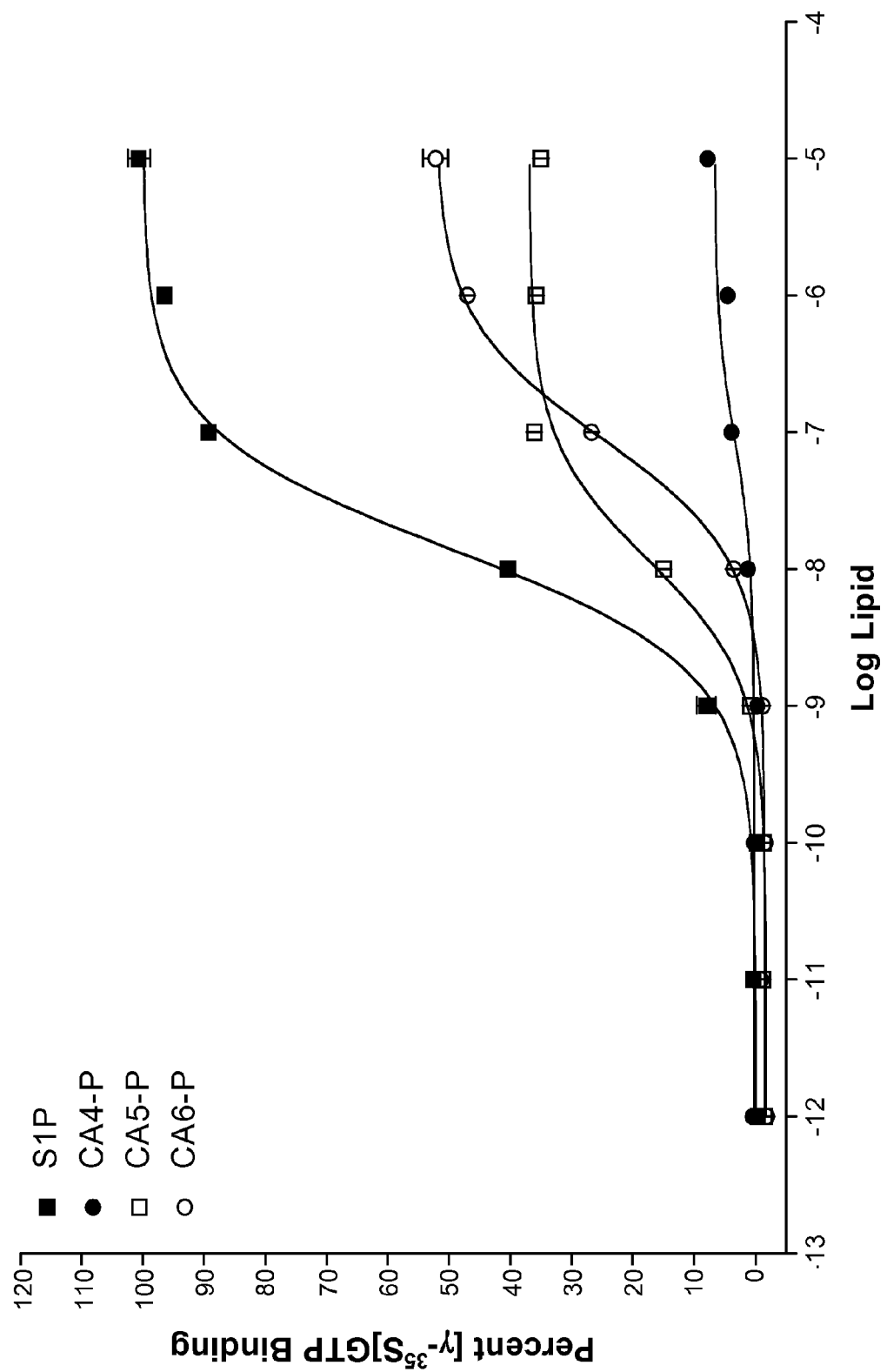
FIG. 6 graphically illustrates the results of a broken cell GTPγ$^{35}$S binding assay for the human $S1P_1$ receptor, testing S1P and three other compounds. Compound 'CA5-P' is VPC01211. Compounds VPC01214 (CA6-P) and VPC01222 (CA4-P) are the corresponding cyclohexyl and cyclobutyl compounds. The ordinate represents percent GTPγ$^{35}$S binding and the abscissa represents log molar concentration of lipid.

VPC01211 (CA5-P) as well as the cyclohexyl (CA6-P) analogs are partial agonists at the S1P$_1$ receptor (FIG. 6), inactive at the S1P$_2$ (FIGS. 7 and 8) and S1P$_3$ receptor (FIG.

Figure 10:
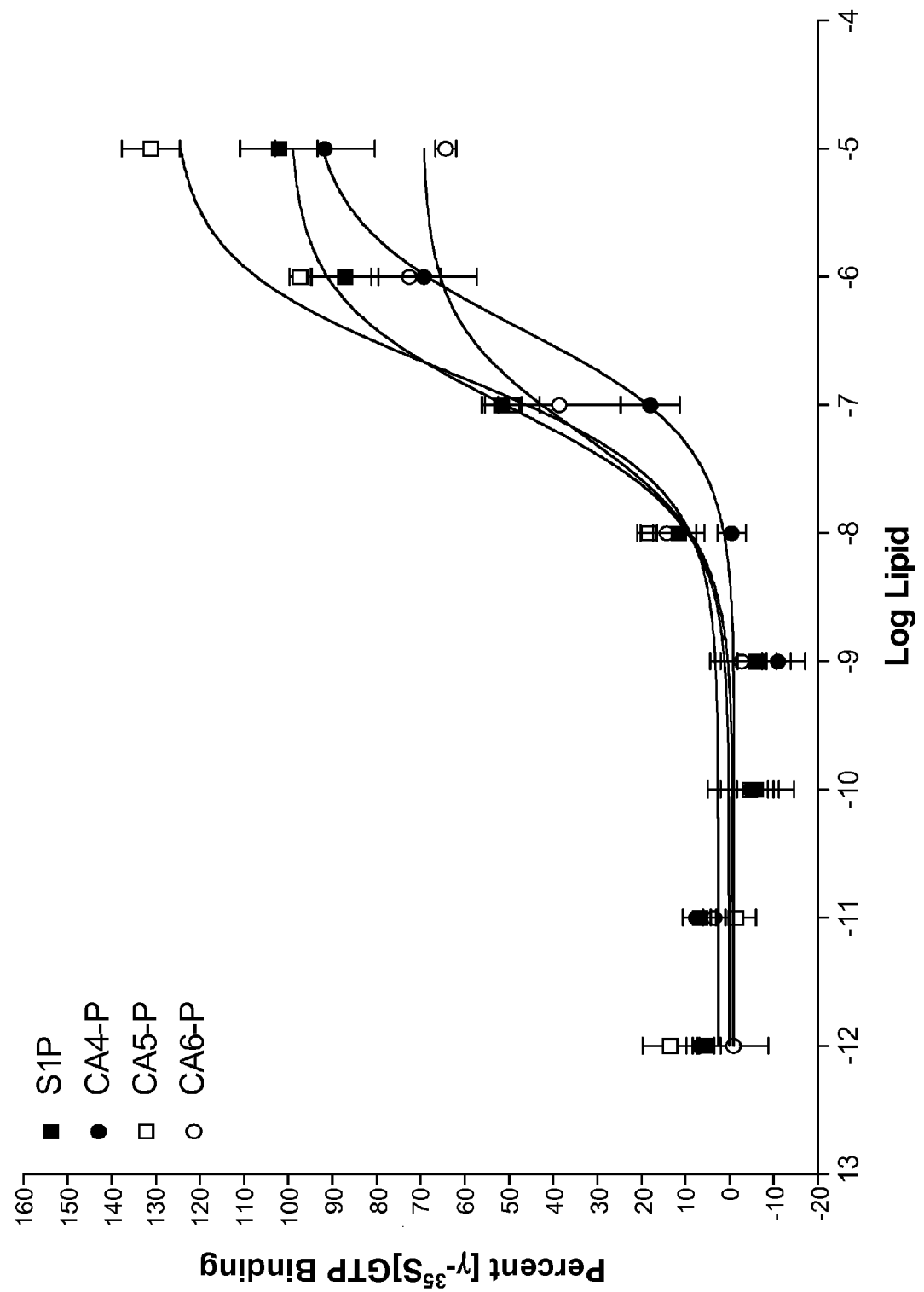
FIG. 10 graphically illustrates the results of a broken cell GTPγ$^{35}$S binding assay for the human $S1P_4$ receptor. Compound 'CA5-P' is VPC01211. Compounds CA6-P and CA4-P are the corresponding cyclohexyl and cyclobutyl compounds.
Figure 11:
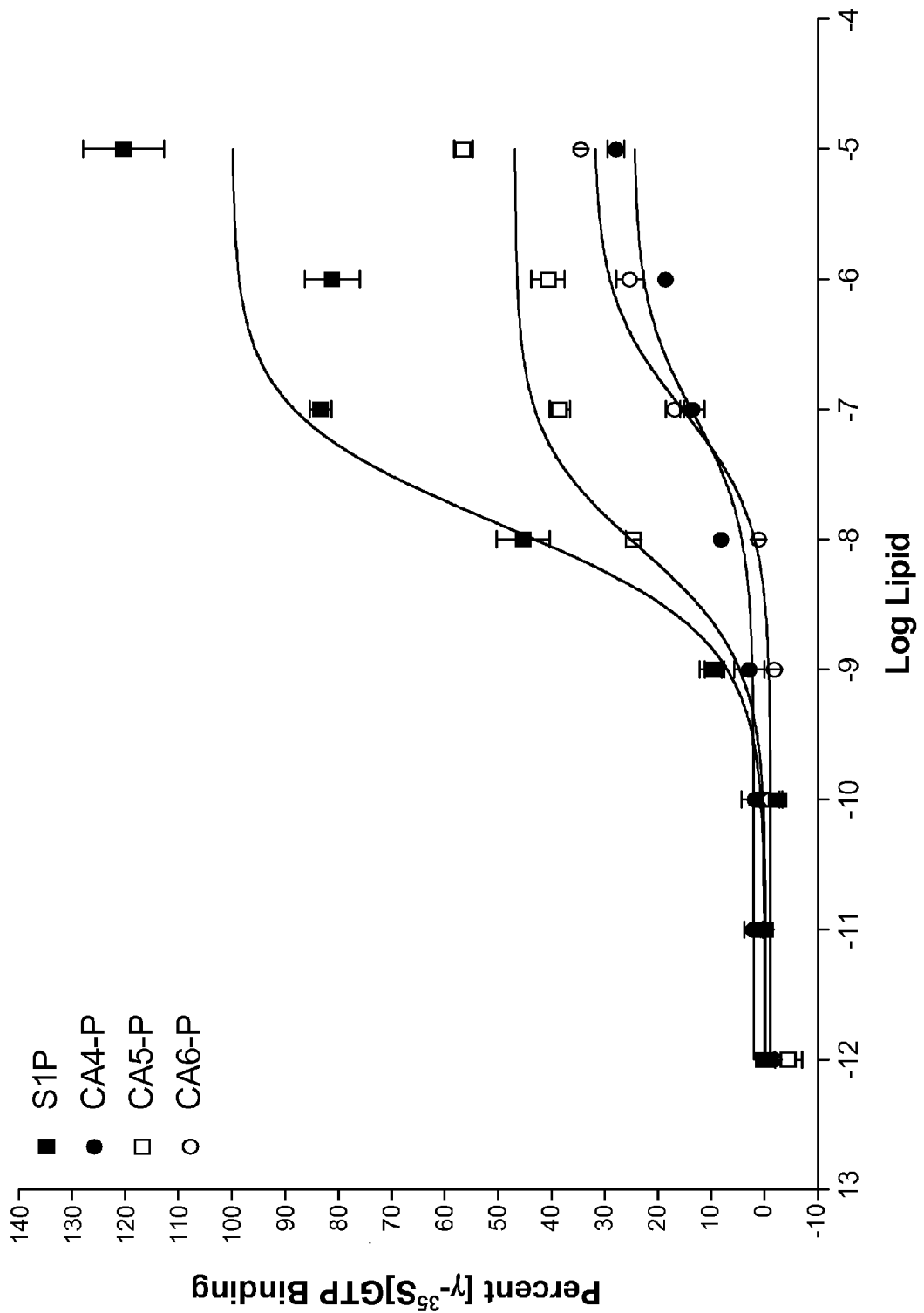
FIG. 11 graphically illustrates the results of a broken cell GTPγ$^{35}$S binding assay for the human $S1P_5$ receptor. Compound 'CA5-P' is VPC01211. Compounds CA6-P and CA4-P are the corresponding cyclohexyl and cyclobutyl compounds.
Figure 12:
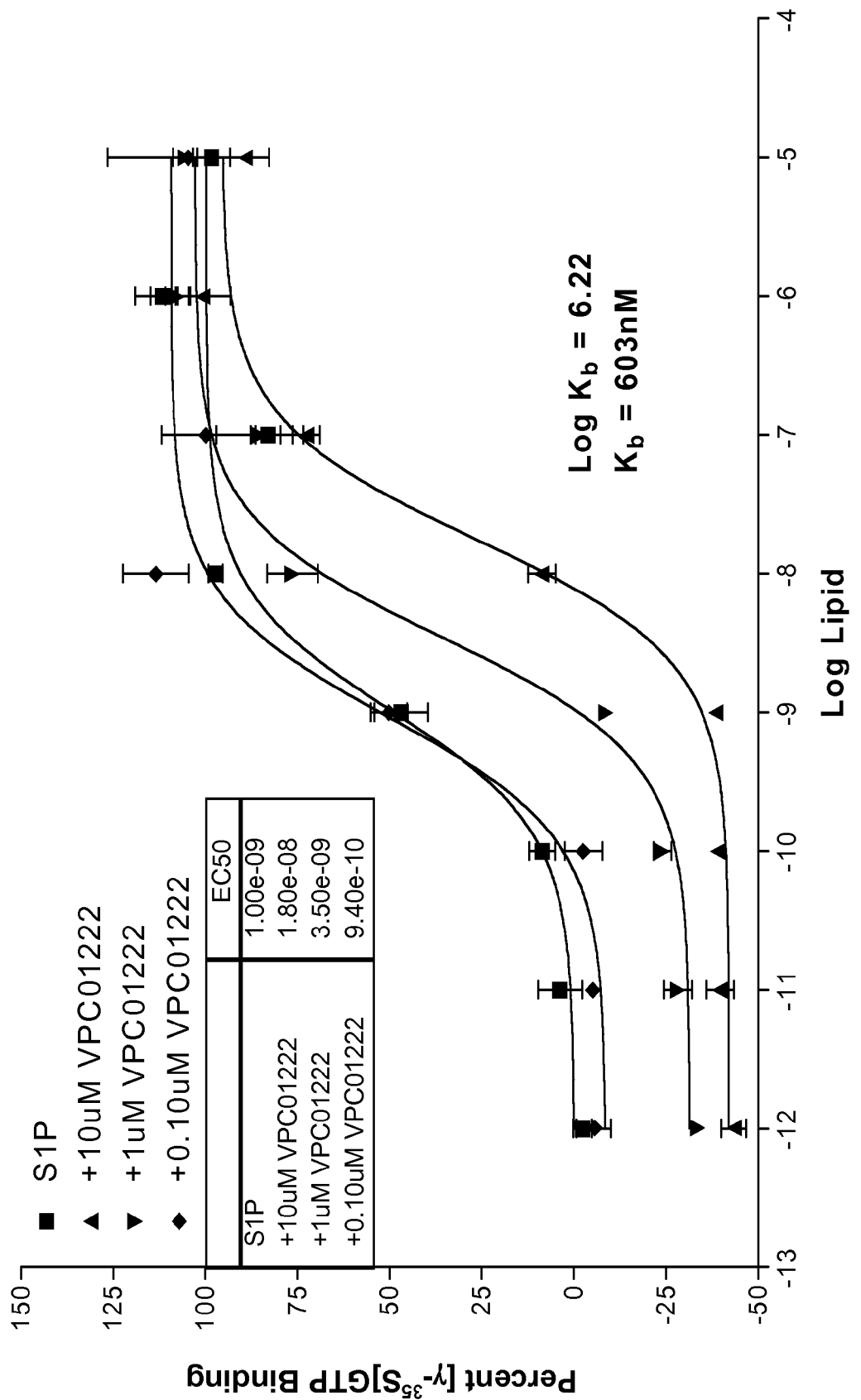
FIG. 12 is an illustration of a Schild plot for the results of S1P dose response curves at the human $S1P_3$ receptor, at the indicated concentrations of test compound VPC01222. The rightward shifts in the S1P dose response curves indicate that VPC01222 is acting as a surmountable antagonist at this receptor type.
Figure 13:
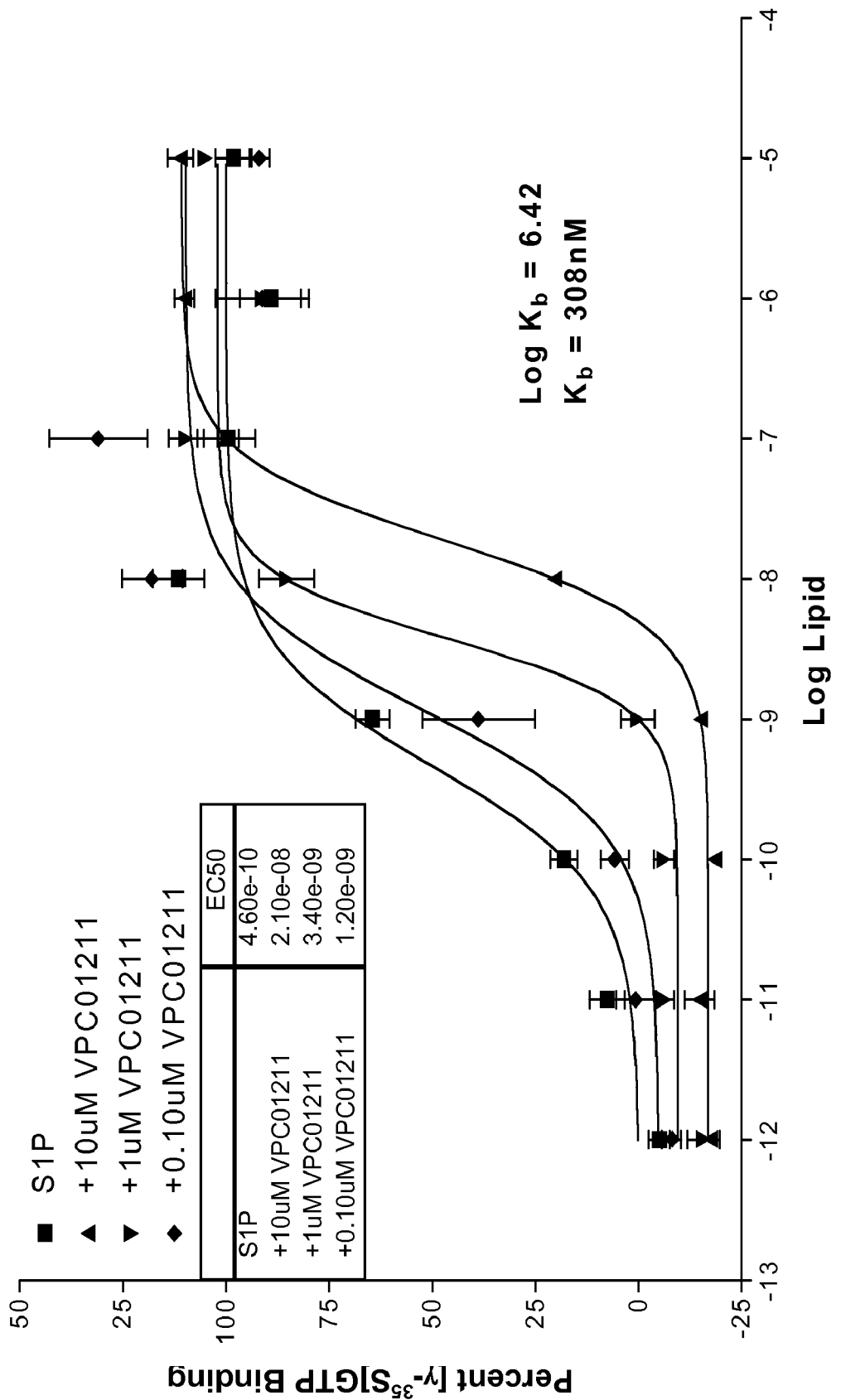
FIG. 13 is an illustration of a Schild plot for the results of S1P dose response curves at the human $S1P_3$ receptor, at the indicated concentrations of test compound VPC01211. The rightward shifts in the S1P dose response curves indicate that VPC01211 is acting as a surmountable antagonist at this receptor type.
Figure 14:
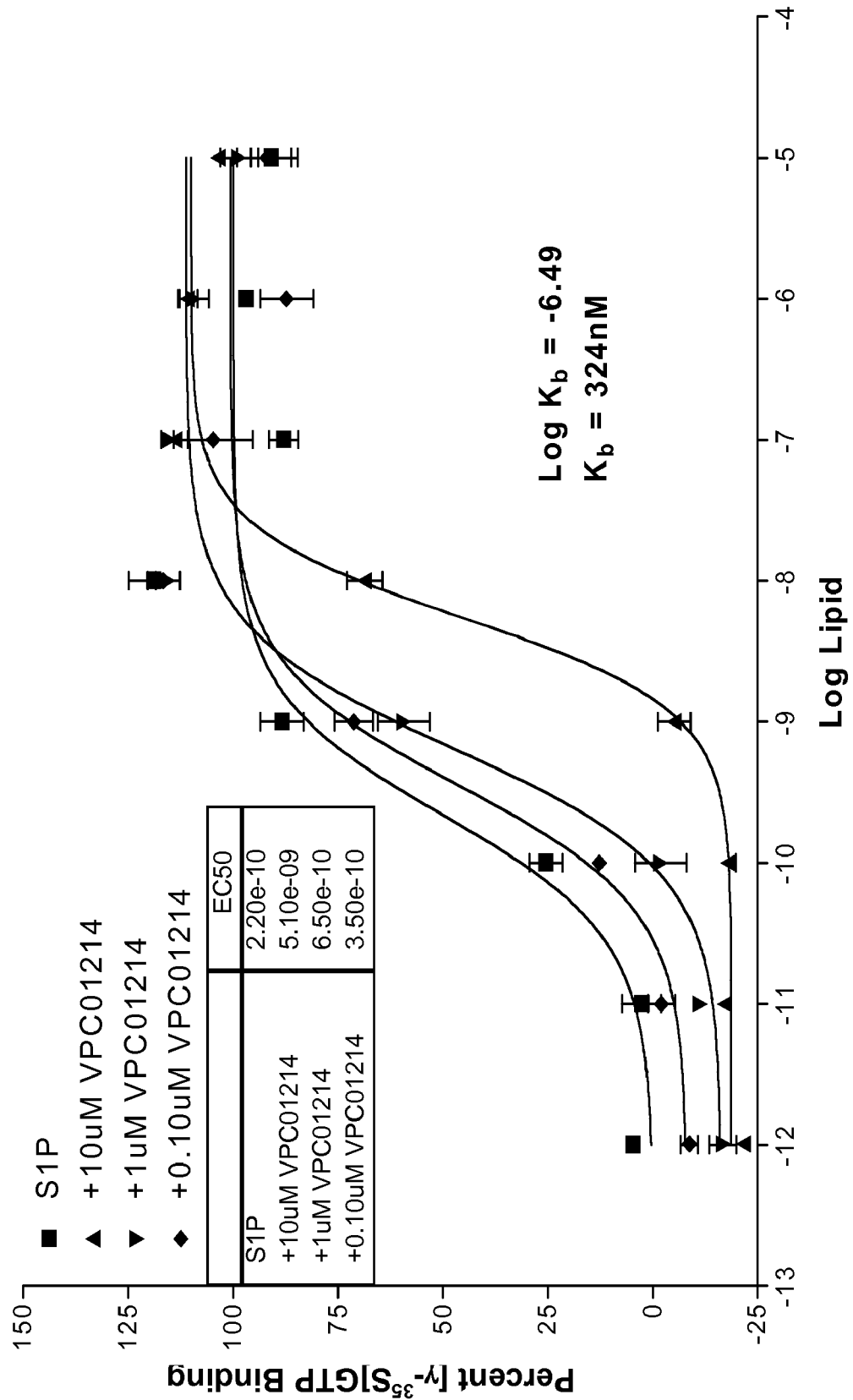
FIG. 14 is an illustration of a Schild plot for the results of S1P dose response curves at the human $S1P_3$ receptor, at the indicated concentrations of test compound VPC01214. The rightward shifts in the S1P dose response curves indicate that VPC01214 is acting as a surmountable antagonist at this receptor type.
Figure 15:
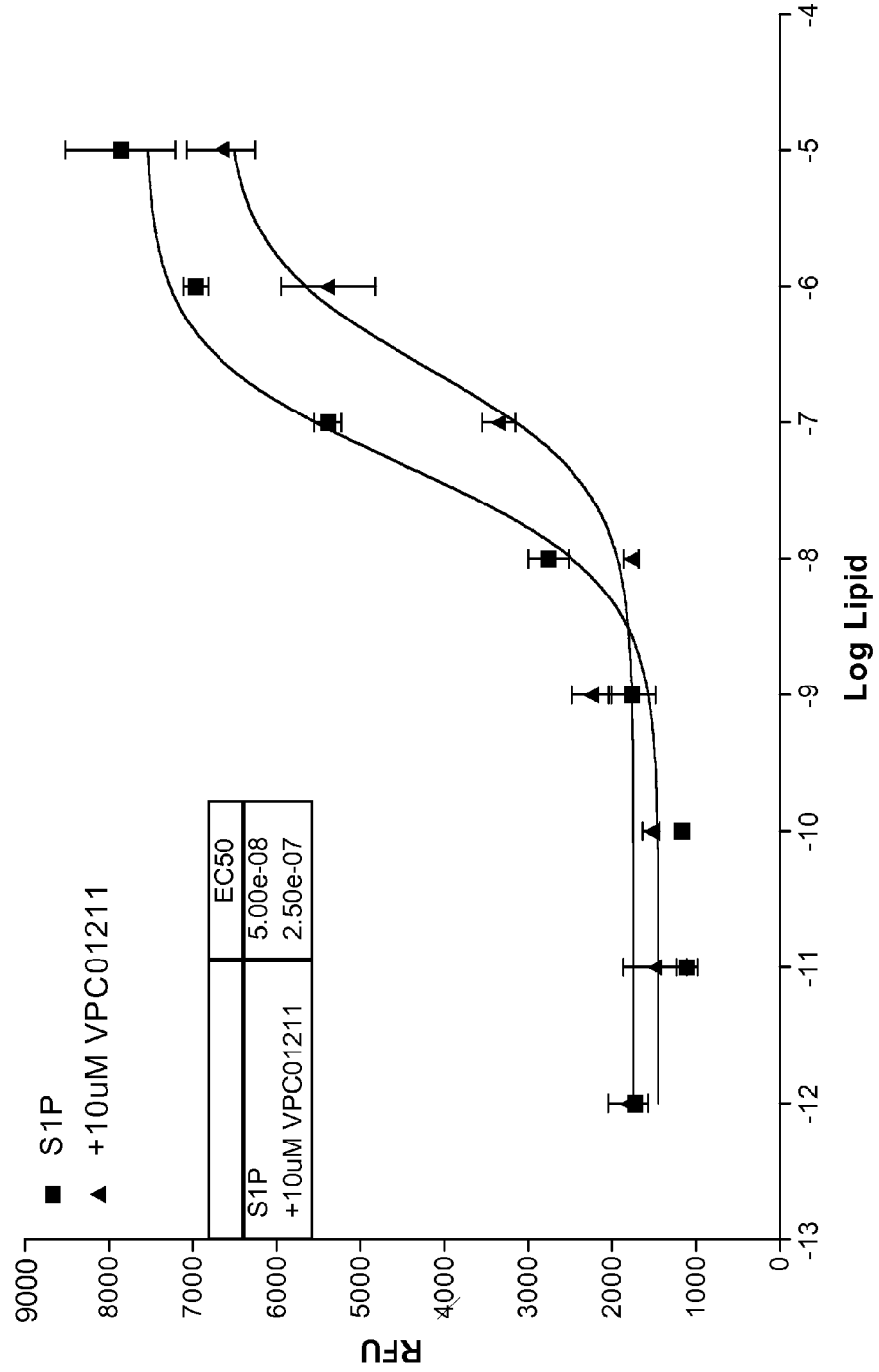
FIG. 15 is an illustration of the result of a calcium mobilization assay in T24 cells overexpressing the human $S1P_3$ receptor in response to $S1P_3$ and S1P in the presence of 10 μM VPC01211. The rightward shift indicates, surmountable antagonism by VPC01211 at the $S1P_3$ receptor.

9). These compounds are full agonists at the $S1P_4$ receptor (FIG. 10) and partial agonists at the $S1P_5$ receptor (FIG. 11). The cyclobutyl compound (CA4-P) has very little agonist activity at the $S1P_1$ receptor, but otherwise activity similar to the cyclopentyl and cyclohexyl compounds.

Figure 16:
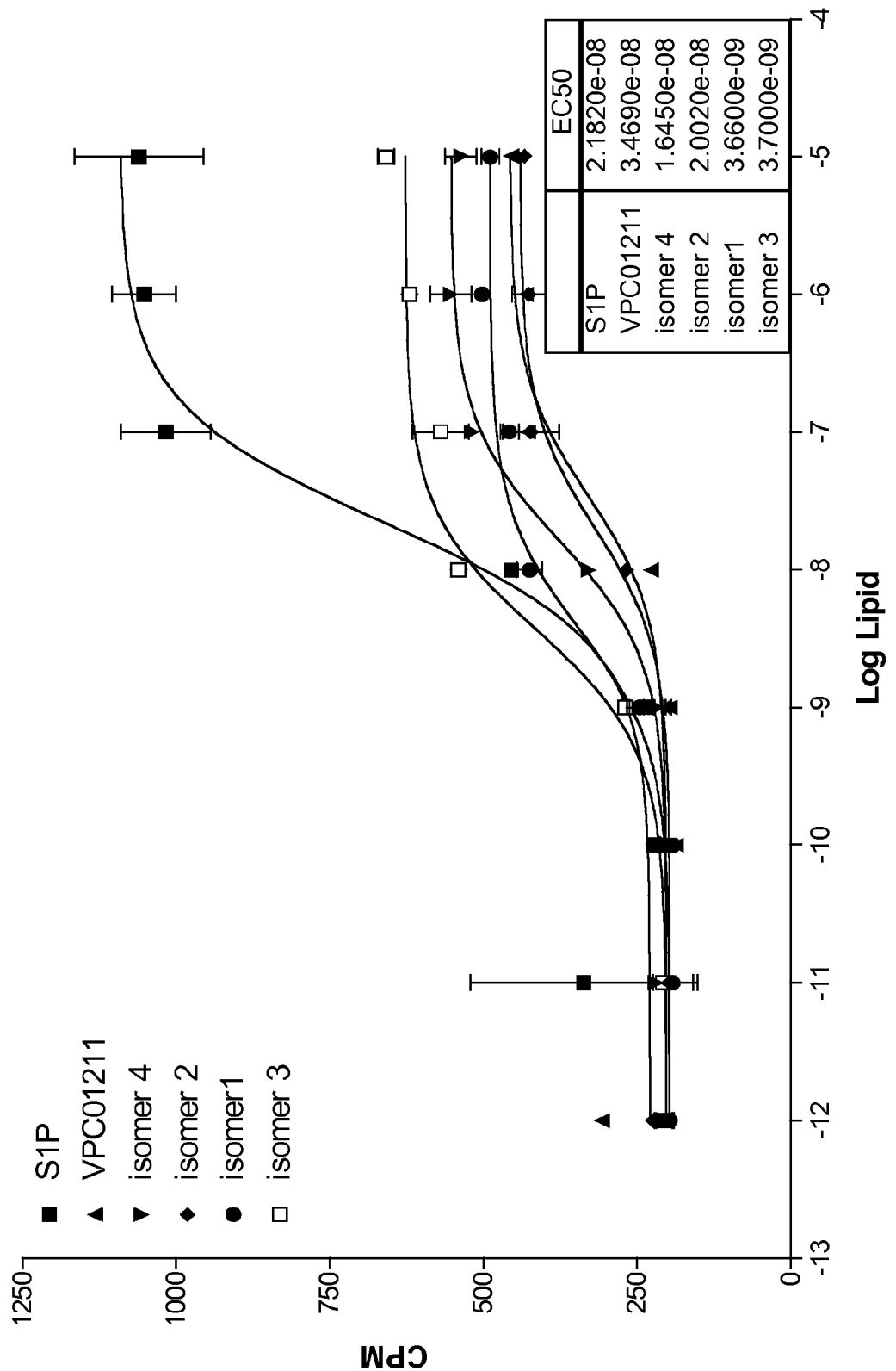
FIG. 16 is an illustration of the ability of the phosphorylated isomers VPC01211 (phosphorylated VPC01091) to agonize the $S1P_1$ receptor.

Sphingosine 1-phosphate (SIP), VPC01211 (phosphorylated VPC01091) and the four component isomers of VPC01211 were assessed at the recombinant human S1P type 1 ($S1P_1$) receptor (FIG. 16). The assay was performed as described in Davis, M. D., J. J. Clemens, T. L. Macdonald and K. R. Lynch (2005) "S1P Analogs as Receptor Antagonists" Journal of Biological Chemistry, vol. 280, pp. 9833-9841. The rank order potency ($EC_{50}$) of the compounds in this experiment was: isomer 1>isomer 3>isomer 4>isomer 2>S1P>VPC01211. The isomers were prepared by chemical phosphorylation of each of the individual isomers of VPC01091.

Figure 17:
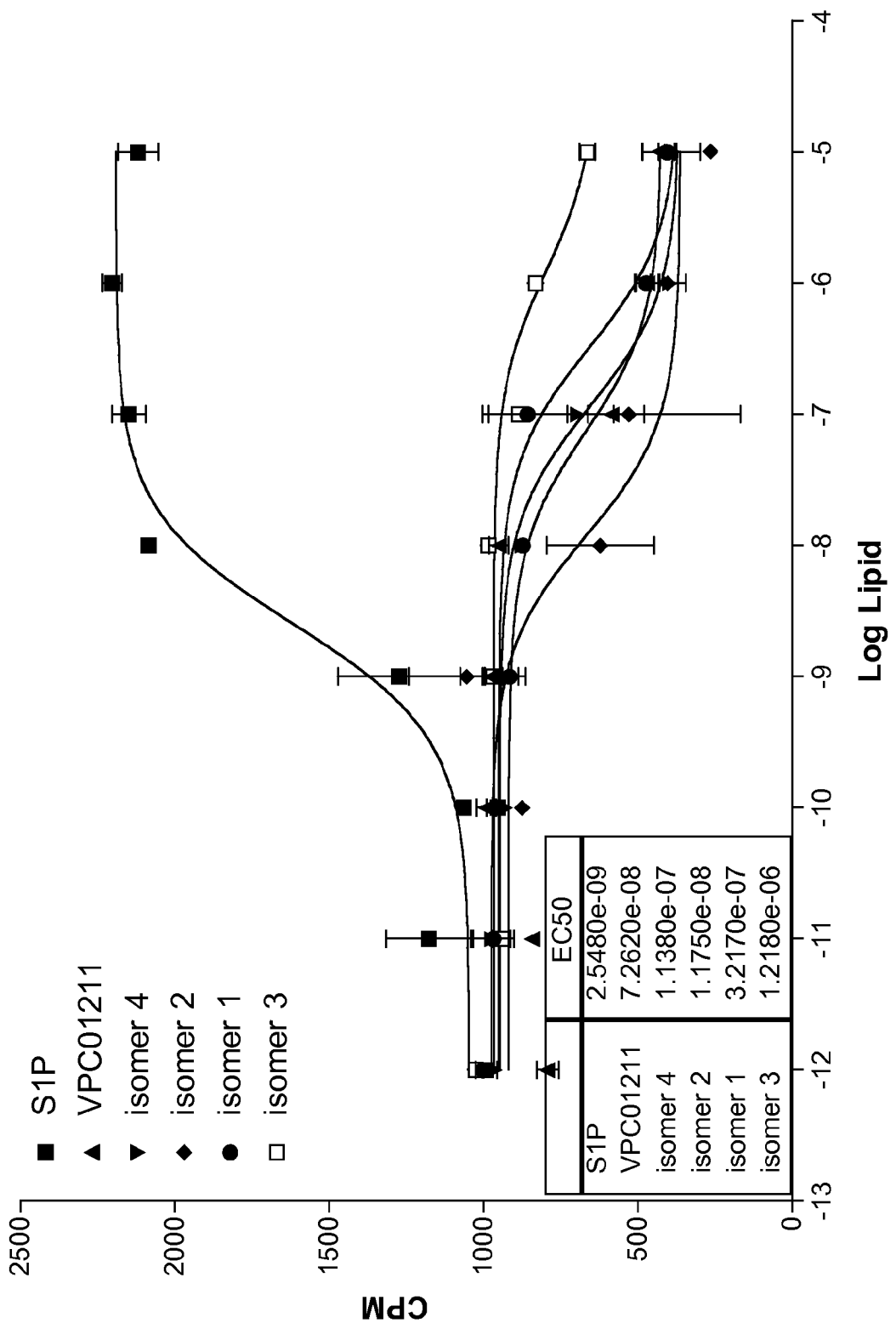
FIG. 17 is an illustration of the ability of the phosphorylated isomers VPC01211 (phosphorylated VPC01091) to agonize the $S1P_3$ receptor.

Sphingosine 1-phosphate (SIP), VPC01211 (phosphorylated VPC01091) and the four component isomers of VPC01211 were assessed at the recombinant human S1P type 3 ($S1P_3$) receptor (FIG. 17). The assay was performed as described in Davis, M. D., Clemens, T. L. Macdonald and K. R. Lynch (2005) "S1P Analogs as Receptor Antagonists" Journal of Biological Chemistry, vol. 280, pp. 9833-9841. The rank order potency (EC50) of the compounds in this experiment was: S1P>isomer 2>VPC01211>isomer 4>isomer 1>isomer 3. The isomers were prepared by chemical phosphorylation of each of the individual isomers of VPC01091.

Example 4

Lymphopenia Assay

Pro-drug compounds (i.e., primary alcohols such as VPC01091) are dissolved in 2% hydroxypropyl beta-cyclodextrin and introduced into mice by oral gavage at doses from 0.01 to 30 mg/kg body weight. After 24 hours (or multiples thereof), the mice are lightly anesthetized and ca. 0.1 ml of blood is drawn from the orbital sinus. The number of lymphocytes (in thousands per microliter of blood; normal is 4-11) is determined using a Hemavet blood analyzer. In the histogram showing the four isomers of VPC01091, the 100% value for the vehicle treated mouse was 7.5 at 24 hours; at 96 hours it was 5. There were three mice/group, the strain was mixed sv129×C57BL/6. Active compounds (e.g., VPC01211) are dissolved in acidified DMSO at 20 mM, and diluted 1:20 into 2% hydroxypropyl beta-cyclodextrin in water with mixing. This solution is introduced into mice by intraperitoneal (i.p.) injection at doses of 0.01-10 mg/kg body weight.

Figure 3:
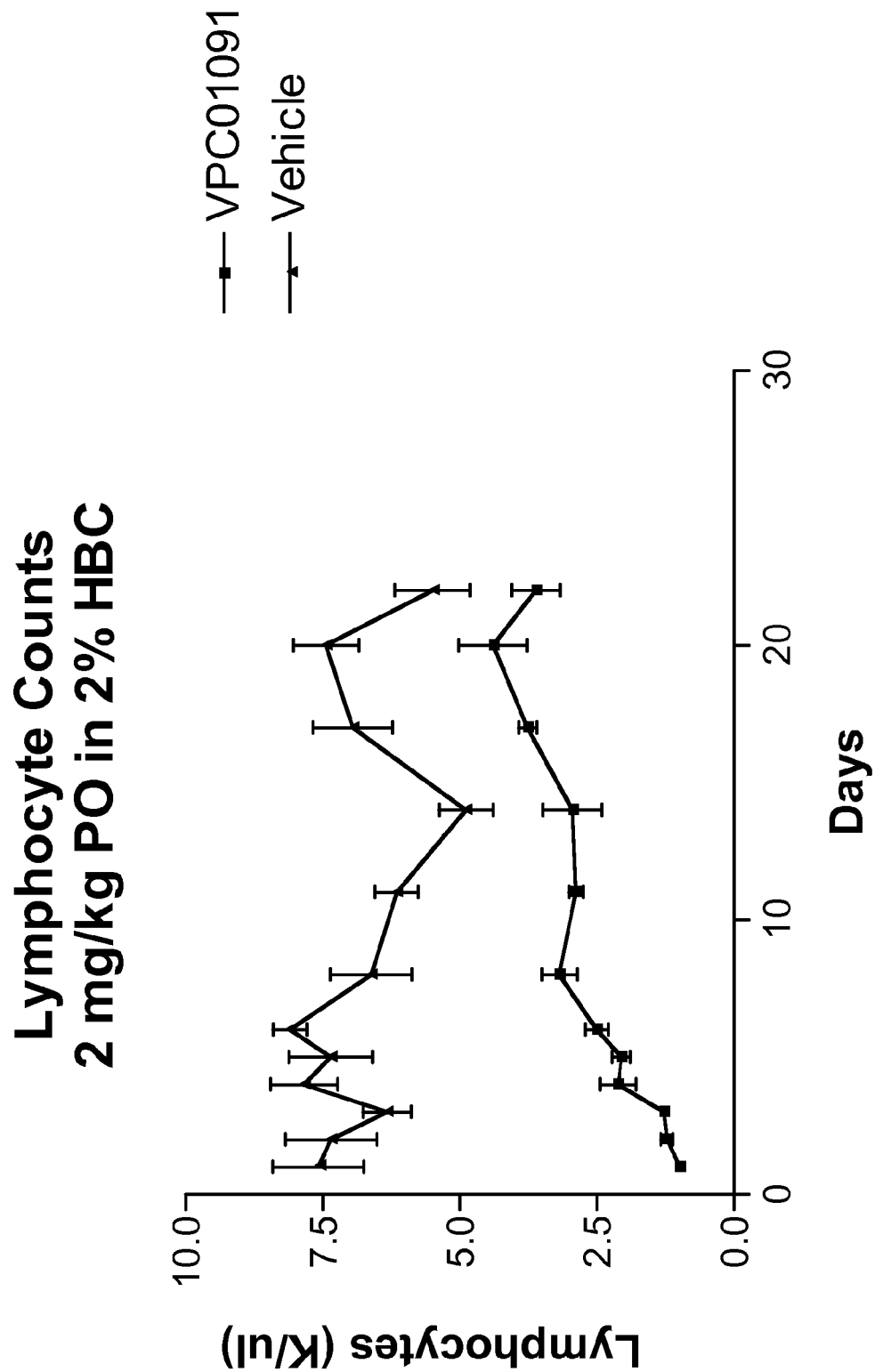
FIG. 3 graphically illustrates total blood lymphocyte count following administration of a single dose of VPC01091 or vehicle to mice. Five mice per group, male, 10-11 week old sv129×C57B1/6 strain. The ordinate represents lymphocytes in K/µl. The abscissa represents time in days.

When dissolved in 2% aqueous hydroxypropyl beta-cyclodextrin (vehicle) and administered to mice orally (gavage), VPC01091 evokes a profound, long lasting lymphopenia (FIG. 3). FIG. 3 describes total blood lymphocyte count following single dose of VPC01091 or vehicle. A single $ED_{95}$ dose of VPC01091 can cause lymphopenia for a week or more. Five mice per group, male, 10-11 week old sv129/C57B16 strain.

Figure 4:
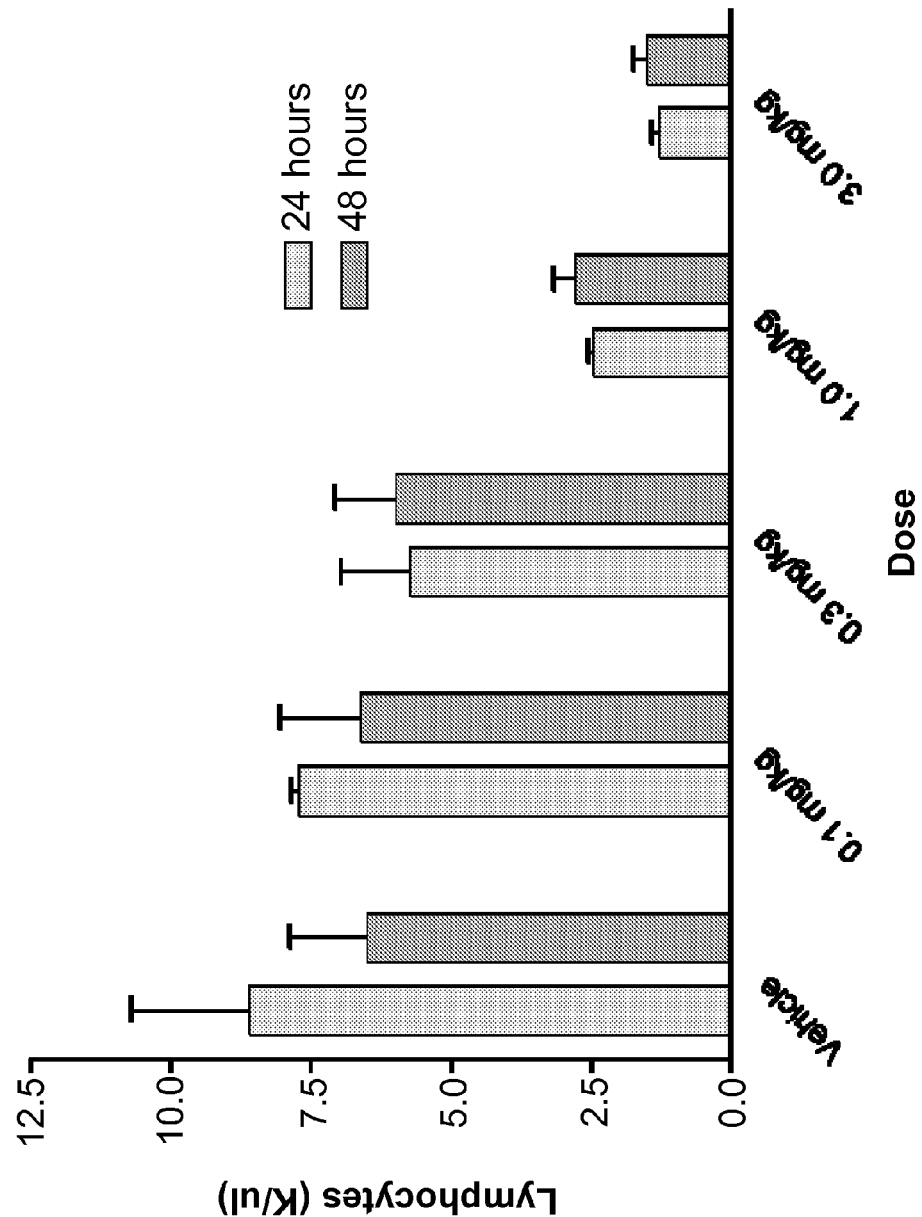
FIG. 4 graphically illustrates the results of a lymphopenia assay following oral administration (gavage) of varied concentrations of VPC01091 (vehicle control, 0.1, 0.3, 1.0, and 3.0 mg/kg) in 2% hydroxypropyl beta-cyclodextrin, 3 mice per group (same strain as in FIG. 3), as measured at 24 (left bar of each group) and 48 hours (right bar of each group).

A dose response curve for VPC01091 in the lymphopenia assay is given as FIG. 4. FIG. 4 graphically summarizes oral administration (gavage) of VPC01091 in 2% hydroxypropyl beta-cyclodextrin, 3 mice per group (same strain as in FIG. 3).

Figure 5:
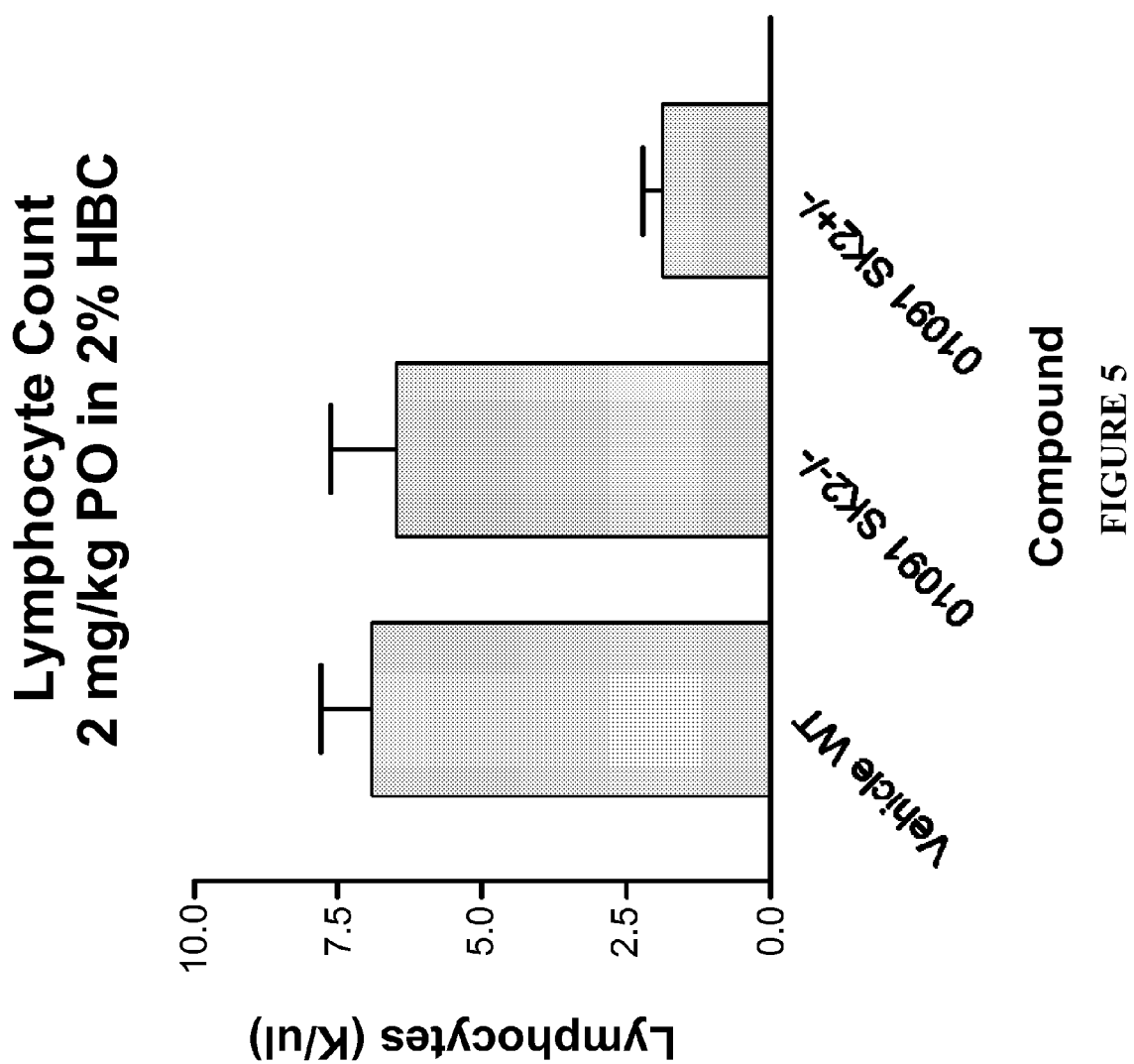
FIG. 5 graphically illustrates total lymphocyte counts (k/µl) 24 hours after a single oral dose of VPC01091 into heterozygous ($SPHK2^{+/tr}$) and homozygous ($SPHK2^{tr/tr}$) mice, wild type mice received vehicle (hydroxypropyl beta-cyclodextrin) alone. The SPHK2 gene was disrupted by insertion of an exon trap element into both alleles.

This phosphorylation of these compounds is thought to be catalyzed in vivo by sphingosine kinase type 2 (SPHK2), which is encoded by the SPHK2 gene in mice. When VPC01091 was introduced into mice without a functional SPHK2 gene, no lymphopenia was observed (FIG. 5).

Figure 18:
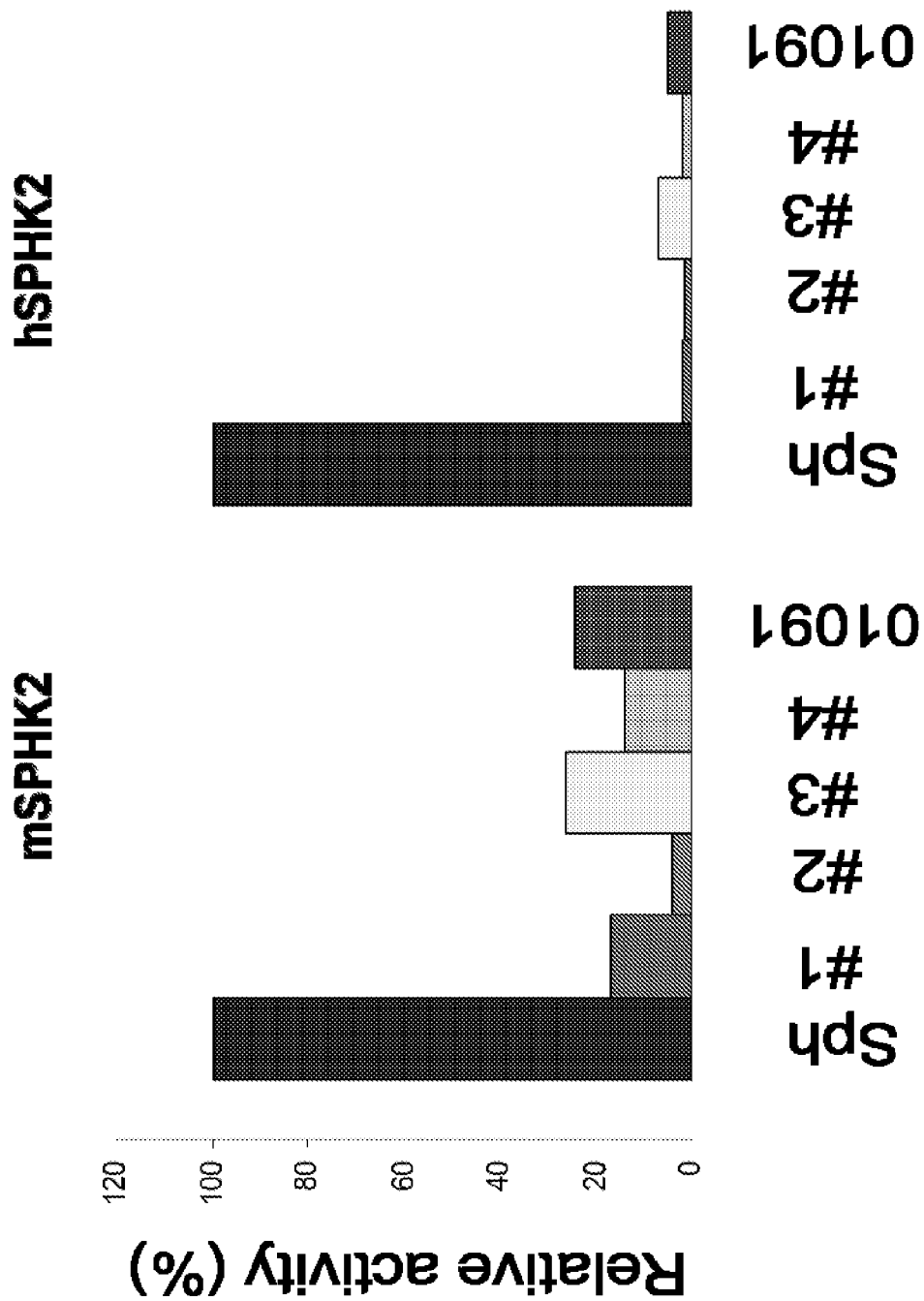
FIG. 18 is an illustration of the SPHK2 activity with the four VPC01091 isomers.

In FIG. 18 the ability of the SPHK2 enzyme to phosphorylate the four VPC01091 isomers is illustrated.

Figure 19:
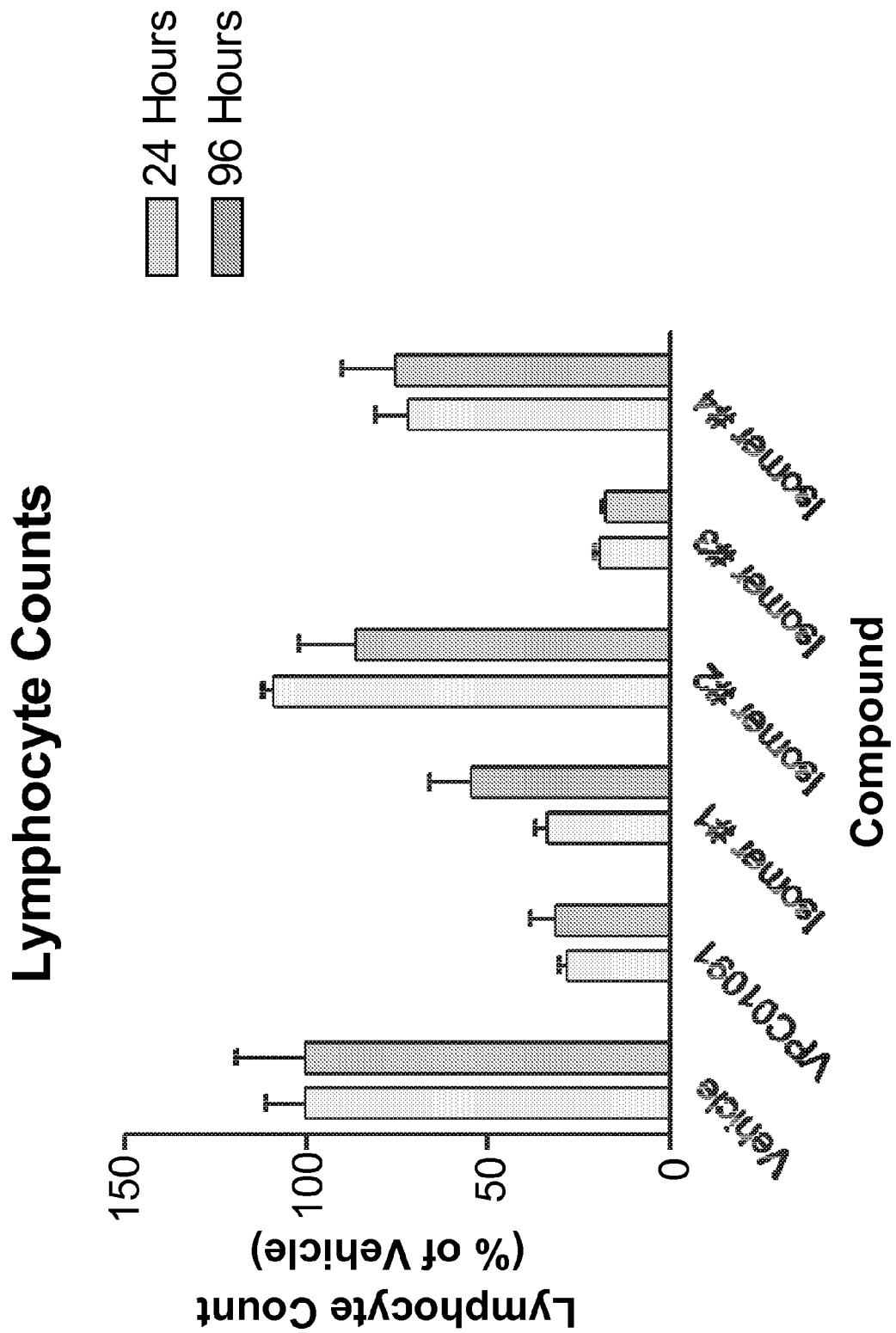
FIG. 19 is an illustration of the graphically illustrates total lymphocyte counts (k/μl) 24 hours (left bar of each group) and 96 hours (right bar of each group) after an oral dose of the VPC01091 isomers is administered to mice.

In FIG. 19 the results of an assay using the phosphorylated isomers of VPC01091 administered via oral gavage are graphically illustrated. The total lymphocyte counts (k/μl) 24 hours and 96 hours after an IV dose of the phosphorylated VPC01091 isomers into mice are reported.

Example 5

Sphingosine Kinase Assay

Recombinant sphingosine kinase type 2 (SPHK2) is prepared by forcing the expression of the mouse or human recombinant enzyme by transfecting the relevant plasmid DNA into HEK293T cells. After about 60 hours, cells are harvested, broken and the non-microsomal (i.e., soluble) fraction is retained. The broken cell supernatant fluid containing the recombinant enzyme is mixed with test compounds (VPC01091, sphingosine, etc.) (5-50 micromolar) and gamma-32P-ATP and incubated for 0.5-2.0 hours at 37° C. The lipids in the reaction mixture are extracted into an organic solvent and displayed by normal phase thin layer chromatography. The radio-labeled bands are detected by autoradiography, scraped from the plate and quantified by scintillation counting. In the histogram shown, sphingosine was present at 15 μM, and the VPC01091 and its isomers at 50 μM, incubation time was 0.5 hours.

Example 6

Calcium Mobilization Assay

Figure 9:
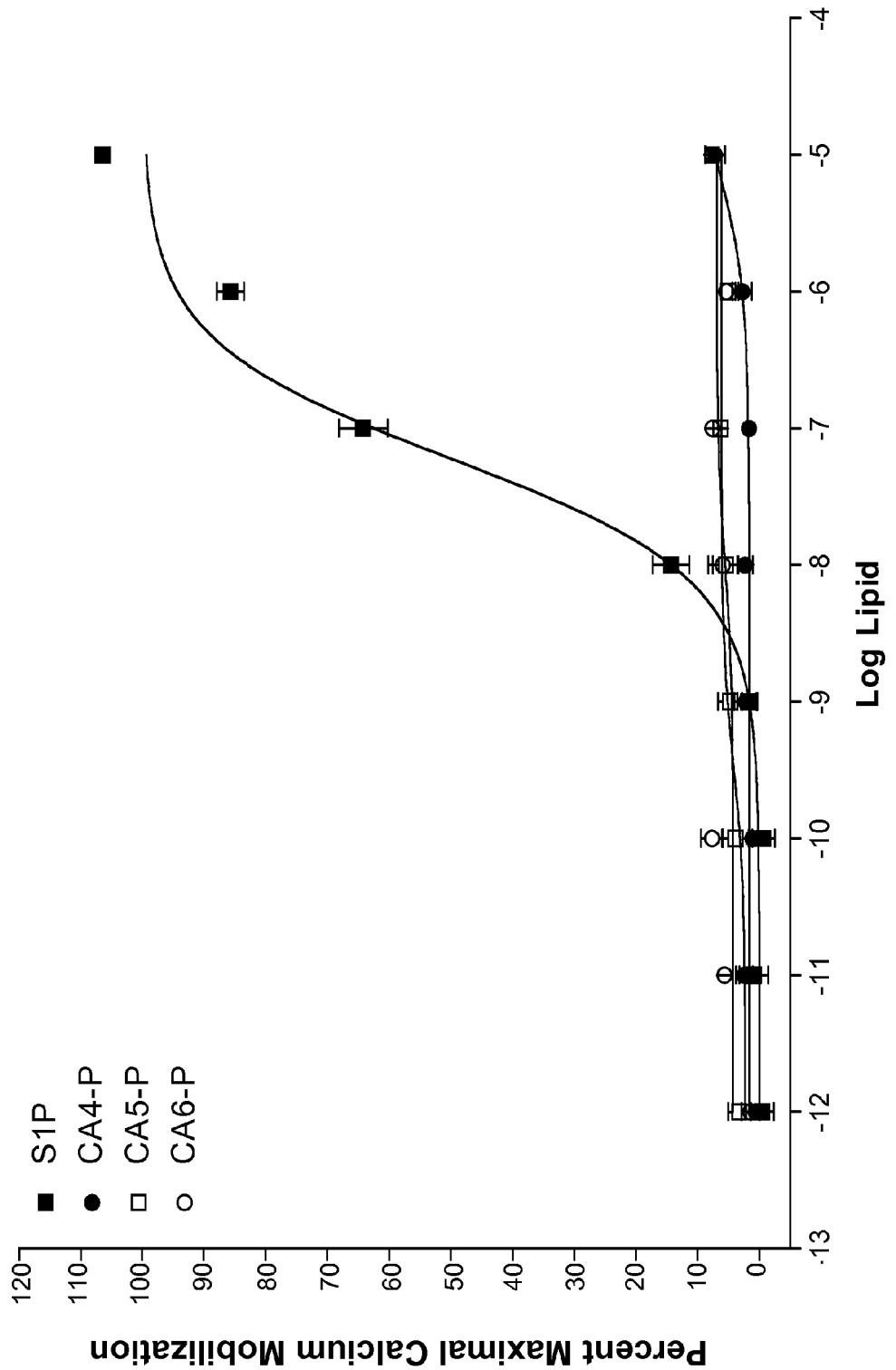
FIG. 9 graphically illustrates the results of a calcium mobilization assay using CHO-K1 cells expressing recombinant human $S1P_3$ receptor. Compound 'CA5-P' is VPC01211. Compounds CA6-P and CA4-P are the corresponding cyclohexyl and cyclobutyl compounds.

Hamster CHOK1 cells were transfected with human $S1P_2$ or human $S1P_3$ receptor DNA and clonal populations that showed ectopic expression of the receptors were isolated and expanded. To measure calcium mobilization in response to agonist stimulation, cells were plated onto a 96 well plate, loaded with the calcium sensing dye Fluo-4AM and cells exposed to various concentrations of agonist for 3-5 minutes. Changes in fluorescence, which correlate with intracellular calcium mobilization, are detected using a FlexStation fluorimeter. Each agonist concentration was tested in triplicate. This protocol is described in greater detail in Davis, M. D., J. J. Clemens, T. L. Macdonald and K. R. Lynch. Sphingosine 1-phosphate analogs as receptor antagonists. J. Biological Chemistry 280, 9833-9841 (2005). The results are illustrated in FIGS. 7 and 9.

Figure 7:
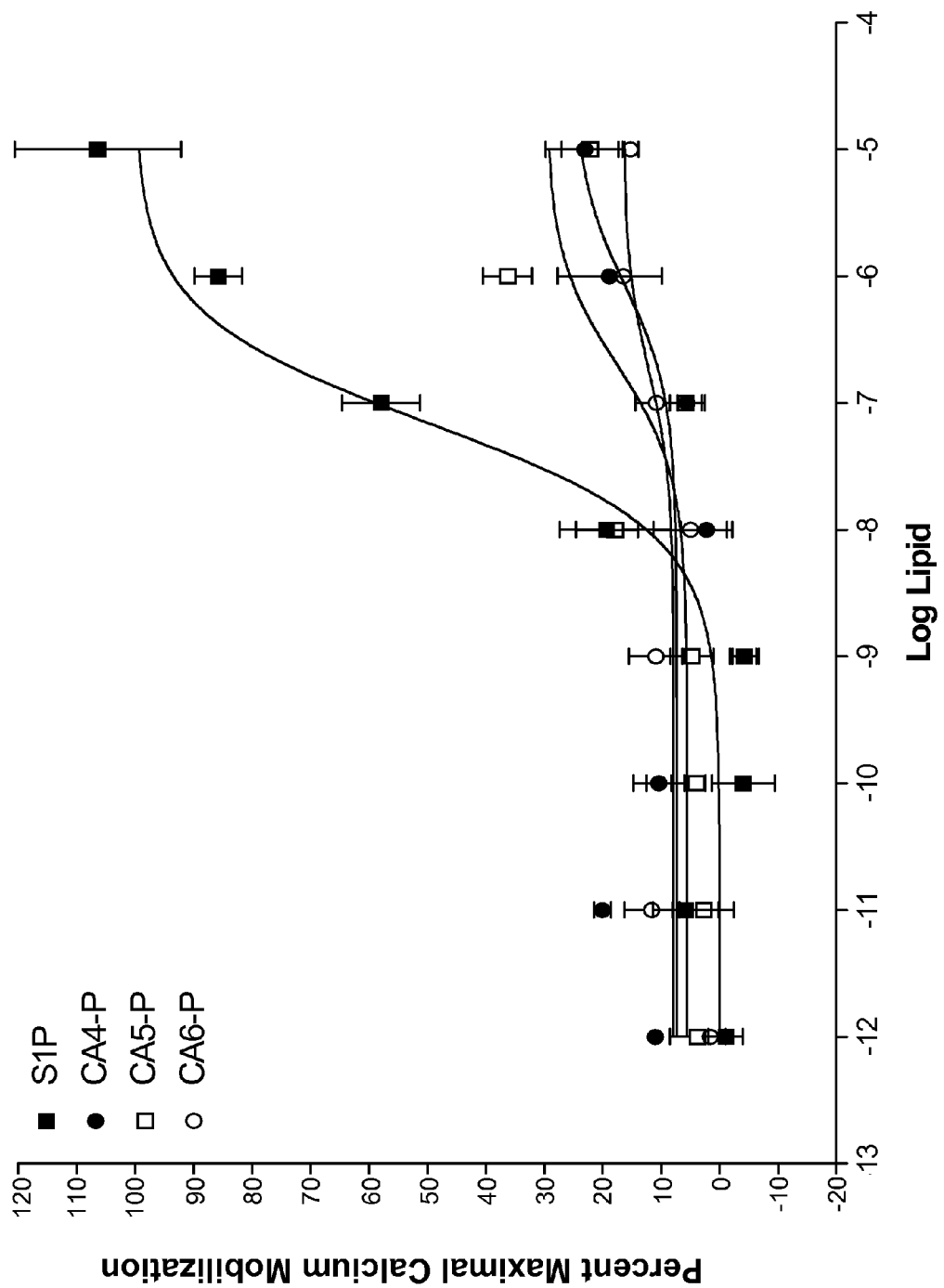
FIG. 7 graphically illustrates the results of a calcium mobilization assay using CHO-K1 cells expressing recombinant human $S1P_2$ receptor. Compound 'CA5-P' is VPC01211. Compounds CA6-P and CA4-P are the corresponding cyclohexyl and cyclobutyl compounds. The ordinate represents percent maximal calcium mobilization and the abscissa represents log molar concentration of lipid.
Figure 8:
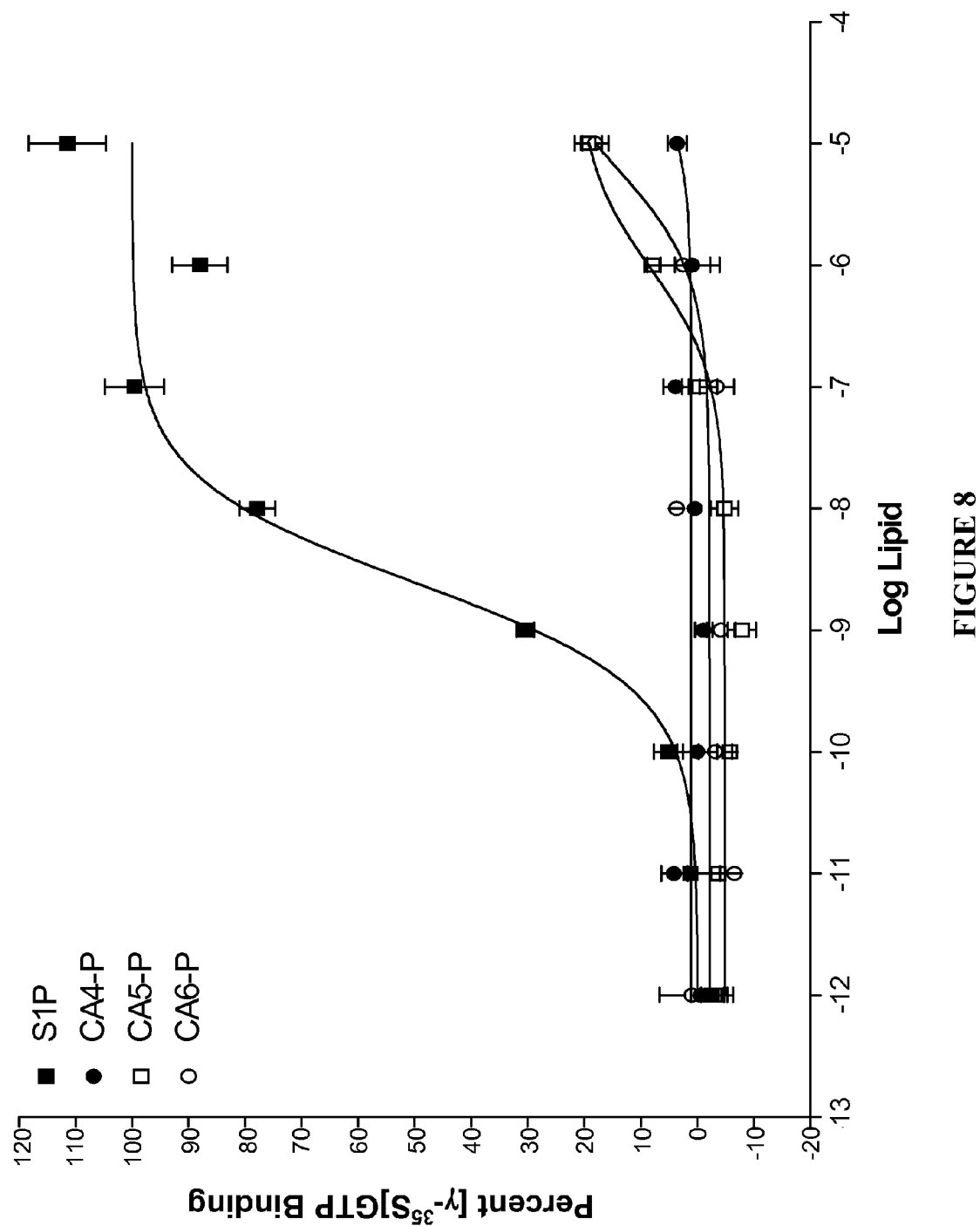
FIG. 8 graphically illustrates the results of a broken cell GTPγ$^{35}$S binding assay for the human $S1P_2$ receptor. Compound 'CA5-P' is VPC01211. Compounds CA6-P and CA4-P are the corresponding cyclohexyl and cyclobutyl compounds. The ordinate represents percent GTPγ$^{35}$S binding and the abscissa represents log molar concentration of lipid.

FIG. 7: CHOK1 cells transfected with $S1P_2$ receptor DNA
FIG. 9: CHOK1 cells transfected with $S1P_3$ receptor DNA Example 7

Heart Rate Assay

Mice were dosed with VPC01091 (intravenous, 3 mg/kg) or vehicle (2% hydroxypropyl beta-cyclodextrin) and heart rate measured at the indicated times post dosing. Heart rate was captured in unrestrained, conscious animals using the ECGenie™ system.

Figure 2:
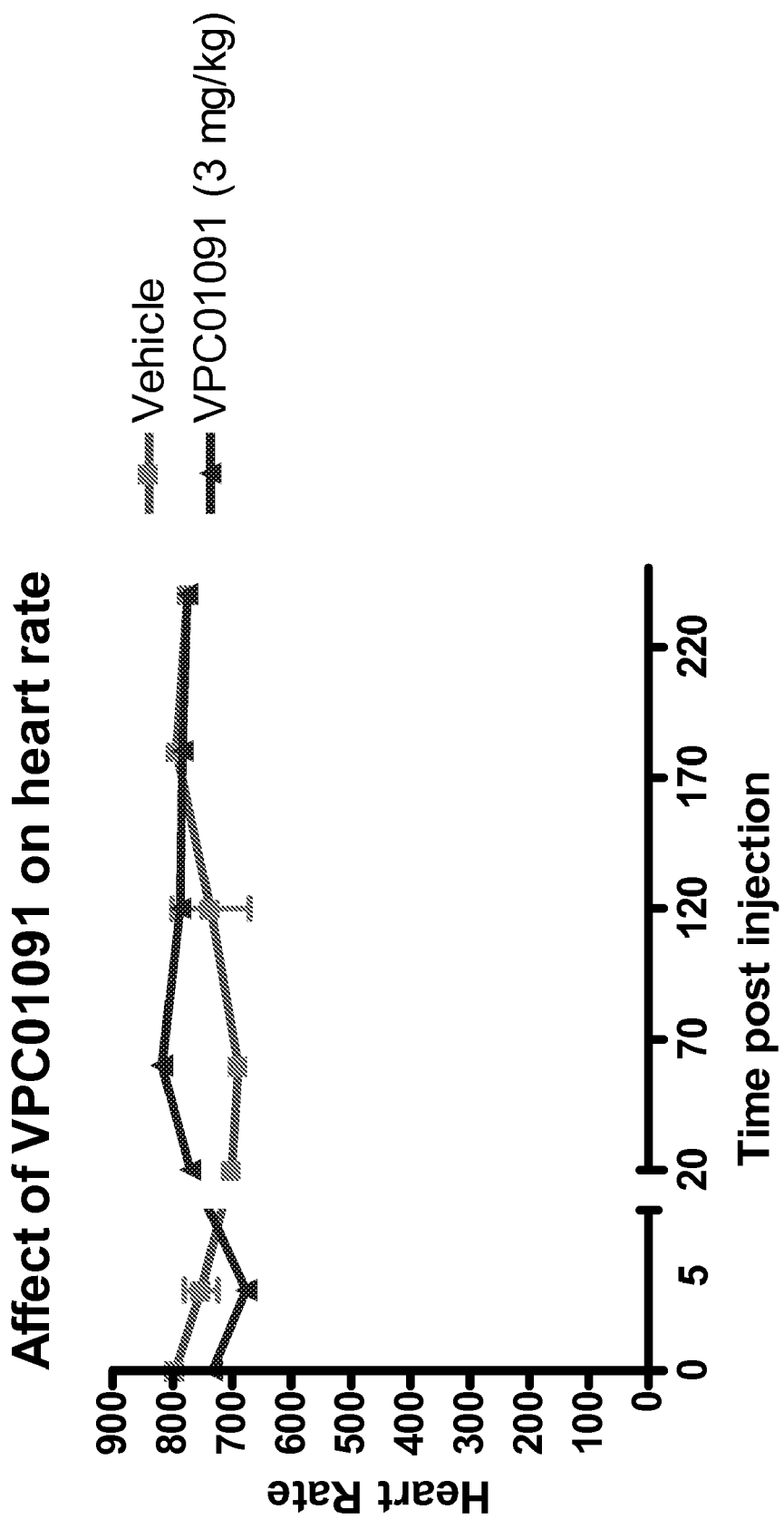
FIG. 2 is a graphical representation of the results of an assay illustrating that compound VPC01091 has no effect on the heart rate of mice. In the assay the test compound was administered via IV Dosing and the vehicle was 2% cyclodextrin.

The results are illustrated in FIG. 2.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

The abbreviations used herein have their conventional meaning within the chemical and biological arts. All publications, patents, and patent documents cited in the specification are incorporated by reference herein, as though individually incorporated by reference. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

We claim:

1. A method for treatment of a pathological condition or symptom in a mammal, wherein the activity of sphingosine 1-phosphate receptors is implicated and agonism of such activity is desired, comprising administering to said mammal an effective amount of a compound having the formula:

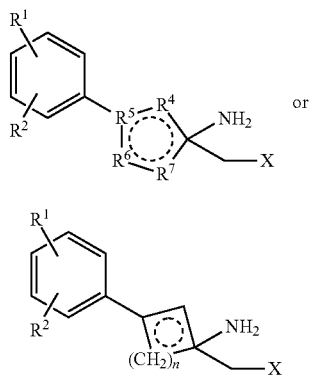

wherein $R^4$ and $R^7$ are independently CH, or $CH_2$; $R^5$ is C, CH, or N, $R^6$ is CH, $CH_2$, O, S or $NR^3$; wherein $R^3$ is hydrogen, or an ($C_1$-$C_{10}$) alkyl group;

X is selected from hydroxyl, phosphate, phosphonate, alpha-substituted phosphonate;

$R^1$ is selected from the group consisting of hydrogen, halo, trifluoromethyl, ($C_1$-$C_{10}$) alkyl, ($C_1$-$C_{10}$) alkyl substituted with halo, hydroxy-, ($C_1$-$C_{10}$) alkoxy, or cyano; and $R^2$ is selected from the group consisting of ($C_1$-$C_{10}$)alkyl, cycloalkyl substituted alkyl, ($C_2$-$C_{20}$)alkenyl, ($C_2$-$C_{20}$) alkynyl, aryl, alkyl substituted aryl, arylalkyl and aryl substituted arylalkyl; wherein one or more of the carbon atoms in the $R^2$ groups can be independently replaced with non-peroxide oxygen, sulfur or $NR^8$; wherein $R^8$ is hydrogen, or an ($C_1$-$C_{10}$) alkyl group;

wherein the alkyl, alkenyl, and alkynyl groups in $R^2$ are optionally substituted with oxo; n is 0, 1, 2 or 3; and ⃝ represents 1,2, or 3, optional double bonds; or a pharmaceutically acceptable salt or ester thereof, wherein the treatment of the pathological condition or symptom comprises altering lymphocyte trafficking.

2. The method of claim 1, comprising administering to said mammal an effective amount of a compound having formula (II):

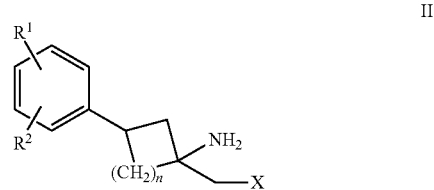

wherein X is selected from hydroxyl, phosphate, phosphonate, and alpha-substituted phosphonate;

wherein $R^1$ is selected from the group consisting of hydrogen, halogens, ($C_1$-$C_6$) alkyl, and halo-, hydroxy-, alkoxy-, cyanosubstituted ($C_1$-$C_6$) alkyl;

$R^2$ is selected from the group consisting of alkyl, alkenyl, alkynyl, alkyl substituted aryl, alkyl substituted cycloalkyl, arylalkyl and arylalkyl substituted aryl; and n is 0, 1, 2 or 3; or a pharmaceutically acceptable salt thereof.

3. The method of claim 1, wherein $R^1$ is fluorine or chlorine.

4. The method of claim 1, wherein X is hydroxy or $OPO_3H_2$.

5. The method of claim 1, wherein X is hydroxy.

6. The method of claim 1, wherein alpha-substituted phosphonate is —$CHFPO_3H_2$, —$CF_2PO_3H_2$, —$CHOHPO_3H_2$, C=$OPO_3H_2$ or —$OPO_2SH_2$.

7. The method of claim 6, wherein alpha-substituted phosphonate is —$CHFPO_3H_2$, —$CF_2PO_3H_2$, —$CHOHPO_3H_2$, or —C=$OPO_3H_2$.

8. The method of claim 1, wherein $R^2$ is alkyl having 5, 6, 7, 8, or 9 carbon atoms.

9. The method of claim 1, wherein $R^2$ is octyl.

10. The method of claim 1, wherein n is 1 or 2.

11. The method of claim 1, wherein $R^2$ group placed para to the cycloalkyl ring.

12. The method of claim 1, wherein the cyclo group has the formula:

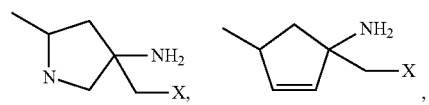

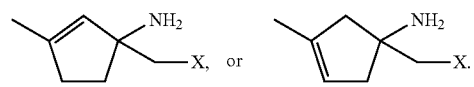

13. The method of claim 1, wherein the $R^1$ group is ortho or meta to $R^2$.

14. The method of claim 1, wherein the $R^2$ group is para to the benzylic cycloalkyl group.

15. The method of claim 1, wherein the compound has the formula:

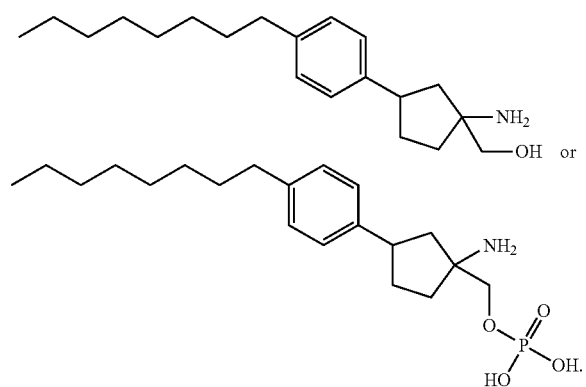

16. The method of claim 1, wherein the compound has the formula:

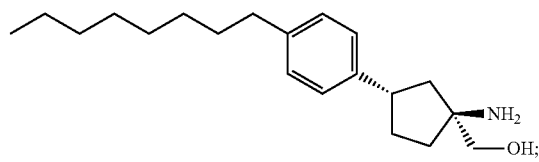

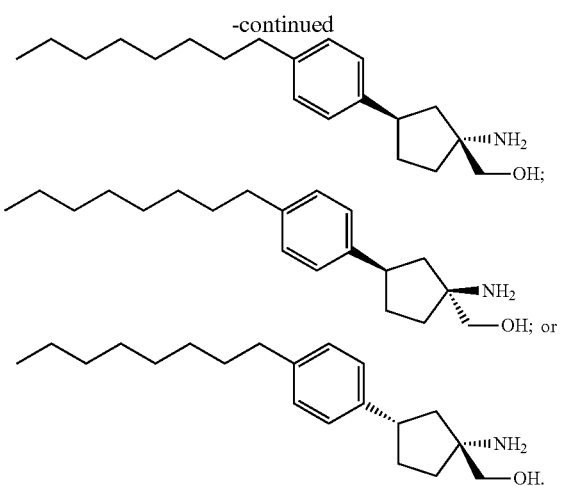

17. The method of claim 1, wherein altering lymphocyte trafficking treats an autoimmune disease selected from the group consisting of uveitis, type I diabetes, rheumatoid arthritis, inflammatory bowel disease, or multiples sclerosis.

18. The method of claim 17, wherein the autoimmune disease is multiple sclerosis.

19. The method of claim 1, wherein altering lymphocyte trafficking provides prolonged allograft survival.

* * * * *